US010350202B2

(12) United States Patent
Jackson

(10) Patent No.: US 10,350,202 B2
(45) Date of Patent: *Jul. 16, 2019

(54) COMPOSITION AND METHOD FOR TREATING SKIN CONDITIONS

(71) Applicant: 442 Ventures, LLC, Louisville, KY (US)

(72) Inventor: J. Mark Jackson, Louisville, KY (US)

(73) Assignee: 442 Ventures, LLC, Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/813,641

(22) Filed: Nov. 15, 2017

(65) Prior Publication Data
US 2018/0117033 A1 May 3, 2018

Related U.S. Application Data

(60) Continuation of application No. 15/679,495, filed on Aug. 17, 2017, now Pat. No. 9,849,123, which is a continuation of application No. 14/918,661, filed on Oct. 21, 2015, now Pat. No. 9,763,930, which is a division of application No. 13/288,814, filed on Nov. 3, 2011.

(60) Provisional application No. 61/410,110, filed on Nov. 4, 2010.

(51) Int. Cl.
| A61K 31/4745 | (2006.01) |
| A61K 31/07 | (2006.01) |
| A61K 31/075 | (2006.01) |
| A61K 31/203 | (2006.01) |
| A61K 31/437 | (2006.01) |
| A61K 31/60 | (2006.01) |
| A61K 45/06 | (2006.01) |
| A61K 9/00 | (2006.01) |
| A61K 31/4436 | (2006.01) |

(52) U.S. Cl.
CPC ........ *A61K 31/4745* (2013.01); *A61K 9/0014* (2013.01); *A61K 9/0019* (2013.01); *A61K 31/07* (2013.01); *A61K 31/075* (2013.01); *A61K 31/203* (2013.01); *A61K 31/437* (2013.01); *A61K 31/4436* (2013.01); *A61K 31/60* (2013.01); *A61K 45/06* (2013.01); *Y02A 50/409* (2018.01)

(58) Field of Classification Search
None
See application file for complete search history.

(56) References Cited

U.S. PATENT DOCUMENTS

| 9,763,930 B2* | 9/2017 | Jackson | A61K 31/07 |
| 9,849,123 B2* | 12/2017 | Jackson | A61K 31/4745 |
| 2004/0097864 A1 | 5/2004 | Dvoretzky et al. | |
| 2005/0226878 A1 | 10/2005 | Tomai et al. | |
| 2006/0287314 A1* | 12/2006 | Waer | A61K 31/519 514/234.5 |
| 2009/0232755 A1* | 9/2009 | Baumann | A61K 8/365 424/59 |

FOREIGN PATENT DOCUMENTS

WO  WO-2008010963 A2 *  1/2008  ........... A61K 9/0014

OTHER PUBLICATIONS

Yin, Clinical Observation on the Efficacy of Topical Imiquimod Cream Combined with Tazarotene Gel in the Treatment of Verruca Plana, The Chinese Journal of Dermatovenereology, 2010, Issue 6, p. 586,589.*
Cotter et al., Treatment of Lentigo Maligna with Imiquimod before Staged Excision, Dermatologic Surgery, vol. 34, No. 2, 17, Dec. 2007 (Dec. 17, 2007), pp. 147-151.*
Modi et al., Combination Therapy with Imiquimod, 5-Fluorouracil, and Tazarotene in the Treatment of Extensive Radiation-Induced Bowen's Disease of the Hands, Dermatologic Surgery, vol. 36, No. 5, May 1, 2010 (May 1, 2010), pp. 694-700.*
Shistik et al., Treatment of locally metastatic melanoma: a novel approach, Journal of Drugs in Dermatology, 2007, vol. 6, No. 8, Aug. 2007 (Aug. 2007), pp. 830-832.*
Zhang et al., The Study of Topical treatment of Verruca Plana with Tazarotene Cream and Imiquimod Cream, The Chinese Journal of Dermatovenereology, vol. 24, issue 3, Mar. 2010.*
Intellectual Property India, First Examination Report issued in corresponding Application No. 4741/DELNP/2013, dated Nov. 16, 2017.
Yuchi C. Chang, et al., "Current and Potential Uses of Imiquimod," Southern Medical Journal, 2005, vol. 98, No. 9, pp. 913-919, ISSN 0038-4348.

* cited by examiner

*Primary Examiner* — Svetlana M Ivanova
(74) *Attorney, Agent, or Firm* — Stites & Harbison, PLLC; Mandy Wilson Decker; Sean P. Ritchie

(57) ABSTRACT

Compositions and methods for treatment of conditions affecting skin and/or mucosal surfaces of a subject that make use of an imidazoquinoline compound and a retinoid agent are described.

20 Claims, 6 Drawing Sheets

COMPOSITION AND METHOD FOR TREATING SKIN CONDITIONS

RELATED APPLICATIONS

This application is a continuation of U.S. patent application Ser. No. 15/679,495, filed on Aug. 17, 2017, which is a continuation of U.S. patent application Ser. No. 14/918,661, filed Oct. 21, 2015, now issued as U.S. Pat. No. 9,763,930, which is division of U.S. patent application Ser. No. 13/288,814, filed Nov. 3, 2011, which claims priority from U.S. Provisional Application Ser. No. 61/410,110 filed Nov. 4, 2010, the entire disclosures of which are incorporated herein by this reference.

TECHNICAL FIELD

The presently-disclosed subject matter relates to the field of medical dermatology, and more specifically to the treatment of skin conditions. In particular, the presently-disclosed subject matter relates to compositions and methods for treating skin conditions, including a combination of an imidazoquinoline compound, and a retinoid agent.

INTRODUCTION

Imidazoquinoline compounds are a family of compounds that have been shown to provide certain beneficial effects, including antiviral and antitumor effects. For example, imiquimod is an immune-modifying agent that, when administered topically to a subject, activates local toll-like receptors to increase interferon and thus the subject's immune response to cells that are over-proliferating due to infection with viral particles or a mutation in the p53 tumor suppressor oncogene. Imiquimod is commercially available as a 3.75% and a 5% cream. It was initially used for anogenital warts, and it has now been FDA-approved for actinic keratoses on the face and scalp, and for superficial basal cell carcinomas. It has also been used off-label for common warts, molluscum contagiosum, keloids, lentigo maligna, SCC in situ, and extramammary Paget's disease.

While treatment of various skin conditions using imiquimod has shown promise, its efficacy is limited. In some cases it proves ineffective because it is unable to effectively penetrate the skin. Indeed, imiquimod is not able to effectively penetrate hyperkeratinized (abnormal and normal) skin, and therefore has a limited ability to have a significant effect in areas where thicker skin is present, e.g., palms, soles, and scalp of a subject. Warts, for example, are often found in areas where thicker skin is present and where imiquimod has limited efficacy. As such, other less-desirable therapies are employed. Such therapies include use of liquid nitrogen, curettage, laser, cautery, etc. which result in significant pain and local destruction of involved and uninvolved tissue. In addition, very few topical therapies have demonstrated adequate benefit to be included as a primary therapy. Furthermore, beneficial effects from imiquimod can require lengthy treatment regimens, sometimes 12-16 weeks of treatment are required to achieve results with facial and genital lesions, which can be unsatisfactory from a treatment standpoint, and which can give rise to patient compliance obstacles.

Retinoid agents are a group of compounds that have been shown to have a variety of beneficial effects and have been used in a number of dermatologic products. For example, tazarotene is a retinoic acid derivative, which acts on the retinoic acid receptor within a cell of a subject to decrease cellular proliferation. Tazarotene is commercially available as a 0.05% and a 0.1% cream or gel. It is used in diseases of hyperkeratinization and epithelial cell proliferation, including pathologies such as acne and psoriasis.

Imidazoquinoline compounds and retinoid agents have been used independently for use in treating various skin conditions. Certain skin conditions have also been treated using alternating applications, at different points in time, e.g., application of imiquimod alone on day 1, and then application of tazarotene alone on day 2; however, such treatments have shown limited efficacy.

Imidazoquinoline compounds and retinoid agents are relatively difficult to formulate. Imiquimod, for example is well known to be a difficult compound to solubilize and therefore stability and compatibility issues have posed problems, not only for finding vehicles that allow imiquimod to be stably-maintained in a formulation for a relevant time period and/or at a relevant temperature, but packaging can even be a concern. Indeed, with regard to packaging, imiquimod formulations are often provided in sachets rather than tubes, because tubes cannot support stabile storage of many imiquimod formulations An imidazoquinoline compound and a retinoid agent have not heretofore been administered simultaneously nor have they been combined and provided together in a single composition. Despite independent use of products, such as commercially-available imiquimod and commercially-available tazarotene, even for use by an individual in alternating applications at different points in time, there has never been a suggestion to combine the compounds into a single composition. Indeed, with the availability of imidazoquinoline compounds and retinoid agents in separate commercial products, and in view the notorious solubility challenges associated with imidazoquinoline compounds, which would call into question the ability to provide a compatible and stable composition including both an imidazoquinoline compound and a retinoid agent, there was no reason to attempt such a combination.

SUMMARY

The present inventor contemplated the simultaneous administration of an imidazoquinoline compound with a retinoid agent, such as by using a composition of the presently-disclosed subject matter. Such a composition was contemplated to achieve beneficial results as compared to the administration of an imidazoquinoline compound or a retinoid agent alone or in alternating treatments at different points in time. Without wishing to be bound by theory or mechanism, it is contemplated that the retinoid agent of the compositions disclosed herein, with the ability to normalize hyperkeratinization, can facilitate penetration of active agents delivered therewith. As further contemplated, an imidazoquinoline compound, such as imiquimod, has penetration limitations that can be overcome by co-administration with a retinoid agent.

As noted herein below, in providing a single composition including both an imidazoquinoline compound and a retinoid agent, unexpected and beneficial results are achieved. Beneficial results include increasing penetration of the imidazoquinoline compound component, which can increase the efficacy of the composition, and which can allow for treatment in locations and on lesions where imidazoquinoline compound and/or retinoid agent treatment was previously ineffective and/or resulted in undue or excessive irritation.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes compositions, pharmaceutical compositions, kits, and methods useful for treating conditions of the skin and/or mucosal surfaces of subjects. The composition of the presently-disclosed subject matter includes an imidazoquinoline compound; and a retinoid agent. Pharmaceutical compositions, methods, and kits of the presently-disclosed subject matter make use of the composition of the presently-disclosed subject matter.

In some embodiments, the imidazoquinoline compound is imiquimod, resiquimod, sotirimod, or mixtures thereof. In some embodiments, the imidazoquinoline compound is imiquimod. In some embodiments, the imidazoquinoline compound is resiquimod. In some embodiments, the imidazoquinoline compound is sotirimod. In some embodiments, the retinoid agent is selected from the group consisting of: retinol, retinal, retinyl acetate, retinaldehyde, retinyl palmitate, retinoic acid, retinyl propionate, retinyl linoleate, dehydroretinol, eretinate, eretrin, motretinide, tazarotene, isotretinoin, tretinoin, adapalene, bexarotene, fenretinide, and alitretinoin. In some embodiments, the retinoid agent is tazarotene. In some embodiments, the imidazoquinoline compound is selected from the group consisting of: imiquimod, resiquimod, and sotirimod; and the retinoid agent is selected from the group consisting of: retinol, retinal, retinyl acetate, retinaldehyde, retinyl palmitate, retinoic acid, retinyl propionate, retinyl linoleate, dehydroretinol, eretinate, eretrin, motretinide, tazarotene, isotretinoin, tretinoin, adapalene, bexarotene, fenretinide, and alitretinoin. In some embodiments, the imidazoquinoline compound is imiquimod and the retinoid agent is tazarotene.

In some embodiments, the composition further comprises additional ingredients. Such ingredients can include, for example, salicylic acid, urea, an alpha hydroxyl acid, and a beta hydroxyl acid. In some embodiments, the composition includes salicylic acid. In some embodiments, the composition includes urea. In some embodiments, the composition includes an alpha hydroxyl acid. In some embodiments, the composition includes a beta hydroxyl acid.

In some embodiments, the composition is provided for the treatment of a condition affecting the skin and/or mucosal surfaces of a subject.

In some embodiments, the composition is provided for the treatment of a condition affecting the skin of a subject. In some embodiments, the composition is provided for the treatment of a condition affecting the mucosal surfaces of a subject.

In some embodiments, the condition is selected from a wart, molluscum contagiosum, a keloid, and a skin cancer.

In some embodiments, the condition is a wart. In some embodiments, the wart is caused by a papillomavirus. In some embodiments, the wart is caused by a human papollomaviruses (HPV). In some embodiments, the wart is selected from: verruca vulgaris (common wart), verruca plana (flat wart) condyloma acuminatum or verruca acuminate (genital wart), and verruca pedis (plantar wart).

In some embodiments, the condition is Molluscum contagiosum.

In some embodiments, the condition is a keloid scar. In some embodiments, the condition is a hypertrophic scar.

In some embodiments, the condition is a skin cancer. In some embodiments, the skin cancer is a premalignant skin cancer. In some embodiments, the skin cancer is a malignant skin cancer. In some embodiments, the skin cancer is selected from melanoma and non-melanoma skin cancers, actinic keratoses, basal cell carcinomas, squamous cell carcinoma-in-situ or Bowen's disease, melanoma in-situ, and other unresectable carcinomas. In some embodiments, the skin cancer is actinic keratoses. In some embodiments, the skin cancer is a primary skin cancer. In some embodiments, the skin cancer is a secondary skin cancer. In some embodiments, the skin cancer is selected from: cutaneous T-cell lymphoma, extramammary Paget's disease, lentigo maligna, cutaneous melanoma metastases, and cutaneous leishmaniasis.

In some embodiments, the subject is a human. In some embodiments, the subject is a transplant patient. In some embodiments, the subject is receiving antirejection therapy following a transplant.

In some embodiments, the retinoid agent is provided in the composition at a final concentration between about 1% (wt/wt) and about 0.001% (wt/wt). In some embodiments, the retinoid agent is provided in the composition at a final concentration between about 1% (wt/wt) and about 0.001% (wt/wt). In some embodiments, the retinoid agent is provided in the composition at a final concentration between about 1% (wt/wt) and about 0.025% (wt/wt). In some embodiments, the retinoid agent is provided in the composition at a final concentration between about 0.5% (wt/wt) and about 0.01% (wt/wt).

In some embodiments, the retinoid agent is tazarotene provided in the composition at a final concentration between about 1% (wt/wt) and about 0.001% (wt/wt). In some embodiments, the tazarotene is provided in the composition at a final concentration between about 1% (wt/wt) and about 0.001% (wt/wt). In some embodiments, the tazarotene is provided in the composition at a final concentration between about 1% (wt/wt) and about 0.025% (wt/wt). In some embodiments, the tazarotene is provided in the composition at a final concentration between about 0.5% (wt/wt) and about 0.01% (wt/wt). In some embodiments, the tazarotene is provided at a concentration of about 1% (wt/wt). In some embodiments, the tazarotene is provided at a concentration of about 0.5% (wt/wt). In some embodiments, the tazarotene is provided at a concentration of about 0.1% (wt/wt). In some embodiments, the tazarotene is provided at a concentration of about 0.05% (wt/wt). In some embodiments, the tazarotene is provided at a concentration of about 0.01% (wt/wt). In some embodiments, the tazarotene is provided at a concentration of about 0.005% (wt/wt). In some embodiments, the tazarotene is provided at a concentration of about 0.001% (wt/wt).

In some embodiments, the imidazoquinoline compound is provided in the composition at a final concentration between about 10% (wt/wt) and about 0.1% (wt/wt). In some embodiments, the imidazoquinoline compound is provided in the composition at a final concentration between about 7% (wt/wt) and about 3% (wt/wt).

In some embodiments, the imidazoquinoline compound is imiquimod provided in the composition at a final concentration between about 10% (wt/wt) and about 0.1% (wt/wt).

In some embodiments, the imiquimod is provided in the composition at a final concentration between about 7% (wt/wt) and about 3% (wt/wt). In some embodiments, the imiquimod is provided at a concentration of about 10% (wt/wt). In some embodiments, the imiquimod is provided at a concentration of about 5% (wt/wt). In some embodiments, the imiquimod is provided at a concentration of about 3.75% (wt/wt). In some embodiments, the imiquimod is provided at a concentration of about 1% (wt/wt). In some embodiments, the imiquimod is provided at a concentration of about 0.5% (wt/wt). In some embodiments, the imiquimod is provided at a concentration of about 0.1% (wt/wt).

In some embodiments, the composition allows for increased penetration of the imidazoquinoline compound. In some embodiments, the composition including a combination of the imidazoquinoline compound and the retinoid agent has a synergistic effect.

In some embodiments, the imidazoquinoline compound and the retinoid agent are provided in formulation that includes a solvent. In some embodiments, the solvent includes isostearic acid. In some embodiments, the solvent further includes alcohol, diethyl sebacate, or mineral oil.

In some embodiments, the composition is substantially stable at a temperature of 50° C. for a period of four (4) weeks. In some embodiments, the composition is substantially stable at a temperature of 40° C. for a period of four (4) weeks. In some embodiments, the composition is substantially stable at a temperature of 25° C. for a period of four (4) weeks. In some embodiments, the composition is substantially stable following up to three freeze/warm cycles from −20° C. to 40° C.

In some embodiments, the composition is formulated for topical delivery. In some embodiments, the composition is formulated for intralesional injection.

As noted herein, the presently-disclosed subject matter includes pharmaceutical compositions of the composition described herein, including the compositions as described in this summary and throughout this application.

The presently-disclosed subject matter further includes a kit. Such kits include the compositions as described in this summary and throughout this application, and a device useful for administration of the composition. Such devices can include, for example, a stick, tape, an occlusive applicator, or an occlusive bandage.

The presently-disclosed subject matter further includes a method for the treatment of a condition affecting skin and/or a mucosal surface of a subject. Such methods include use of the compositions as described in this summary and throughout this application. The method includes administering an effective amount of the composition to the subject. In some embodiments, the composition is administered to an affected site on the skin and/or mucosal surface of the subject. In some embodiments, the composition is administered topically. In some embodiments, the composition is administered by intralegional injection.

DESCRIPTION OF EXEMPLARY EMBODIMENTS

Figures 1A, 1B:
FIG. 1A is a picture of a wart on the heel of a subject prior to treatment using a composition of the presently-disclosed subject matter.
FIG. 1B is a picture of the heel of the subject of FIG. 1A following treatment using a composition of the presently-disclosed subject matter.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10"

is also disclosed. It is also understood that each unit between two particular units is also disclosed. For example, if 10 and 15 are disclosed, then 11, 12, 13, and 14 are also disclosed.

The presently-disclosed subject matter includes compositions and methods for using such compositions for the treatment of a condition affecting the skin and/or mucosal surfaces of a subject. Compositions of the presently-disclosed subject matter include an imidazoquinoline compound and a retinoid agent. In some embodiments, the compositions are pharmaceutical compositions. Methods of the presently-disclosed subject matter include administering an effective amount of a composition comprising an imidazoquinoline compound and a retinoid agent to a subject. The presently-disclosed subject matter includes use of the compositions disclosed herein for the treatment of a condition affecting the skin and/or mucosal surfaces of a subject.

The presently-disclosed subject matter overcomes problems associated with past formulations of imidazoquinoline compounds having limited efficacy. The presently-disclosed subject matter allows for the treatment of areas that before would have been too thick or unresponsive to an imidazoquinoline compound alone (or an imidazoquinoline compound and a retinoid agent in alternating doses at different points in time). The presently-disclosed subject matter provides an alternative to destructive and painful therapies, e.g., liquid nitrogen, curettage, laser, cautery, surgical removal, etc. for certain skin conditions.

Furthermore, the composition of the presently-disclosed subject matter can be useful for treating a condition affecting the a mucosal surface of a subject. Heretofore, retinoids, such as tazarotene, have not typically been used on mucosal surfaces due to accompanying irritation. However, as described in the Examples, the compositions of the presently-disclosed subject matter have unexpected superior results that allow for efficacy at lower concentrations of tazarotene than have previously been used commercially. Such low concentrations decrease the likelihood of irritation to the subject such that embodiments of the compositions of the presently-disclosed subject matter are contemplated for use on mucosal surfaces such as the mouth or genitalia. For example, it is contemplated that a composition of the presently-disclosed subject matter could be provided in a cervical cap to treat a viral lesion, without the need to surgically treat the lesion. Surgical treatment of such lesions can involve removal of a portion of the cervix, resulting in severe consequences, such as a difficulty or an inability to maintain a pregnancy.

Without wishing to be bound by theory or mechanism, it is believe that the simultaneous administration of an imidazoquinoline compound and a retinoid agent in the composition described herein allows for increased penetration of the imidazoquinoline compound, thereby increasing the efficacy of the imidazoquinoline compound in locations and on lesions where it was previously ineffective or insufficiently effective. For example, the inability of imiquimod to penetrate hyperkeratinized (abnormal and normal) skin to the toll-like receptors of the dermis has limited its ability to have a significant effect in areas of where thicker skin is present, e.g., palms, soles, and scalp of a subject. Verrucae (warts) are often found on the palms, soles, and in periungual areas where imiquimod is of limited efficacy.

The term "increased penetration," as used herein with reference to penetration of an imidazoquinoline compound, refers to an increase that is affected by the combination of the imidazoquinoline compound with the retinoid agent in accordance with the presently-disclosed subject matter. As such, the increase refers to the penetration of the imidazoquinoline compound to a site of administration, e.g., lesion, when administered without concurrent administration of a retinoid agent, as compared to the penetration of the imidazoquinoline compound to a site of administration when the composition of the presently-disclosed subject matter is administered. Penetration can be assessed, for example, using Franz diffusion cells, as described in the following references, all of which are incorporated herein by this reference: DePaula, Martins, and Bentley, "Development and validation of HPLC method for imiquimod determination in skin penetration studies," *Biomed Chromatogr* 22(12): 1416-23 (2008); Owens M L, Bridson W E, Smith S L, Myers J A, Fox T L, and Wells T M, "Percutaneous penetration of Aldara cream, 5% during the topical treatment of genital and perianal warts," *Prim Care Update Ob Gyns*. 5(4):151 (1998).

As used herein, the term "imidazoquinoline compound" is inclusive of imiquimod (1-(2-methylpropyl)-1H-imidpzo[4,5-c]quinolin-4-amine), resiquimod (4-amino-α, α-dimethyl-2-ethoxymethyl-1H-imidazo[4,5-c]quinoline-1-ethanol), sotirimod (2-methyl-1-(2-methylpropyl)-1H-imidazo[4,5-c][1,5]naphthyridin-4-amine), and analogs thereof. The term "imidazoquinoline compound" is further inclusive of other imidazoquinoline compounds and derivatives thereof known to those of ordinary skill in the art, including those described in Stanley (2002) Clin. Exp. Dermatol. 27(7):571-577; Jones (2003) Curr. Opin. Investig. Drugs 4(2):214-218; and U.S. Pat. Nos. 4,689,338; 5,389,640; 5,268,376; 4,929,624; 5,266,575; 5,352,784; 5,494,916; 5,482,936; 5,346,905; 5,395,937; 5,238,944; and 5,525,612; and U.S. Patent Application Publication Nos. 2008/0213308; 2009/0182004; 2009/0182005; 2011/0217323; 2011/0245289; and 2011/0250237, each of which is incorporated herein by reference. It is noted that imidazoquinoline compounds have utility as toll-like receptor agonists or activators, e.g., TLR-7. In some embodiments, of the presently-disclosed subject matter, compositions can include a toll-like receptor agonist and a retinoid agent. Imiquimod, a compound in the imidazoquinoline family has been shown to display both antiviral and antitumor effects (Diebold et al. "Innate antiviral responses by means of toll-like receptor (TLR)-7-mediated recognition of single-stranded RNA". *Science* 204; 303: 1529-1531; Barnetson et al. "Imiquimod induced regression of clinically diagnosed superficial basal cell carcinoma is associated with early infiltration by CD4 T cells and dendritic cells". *Clin. Exp. Dermatol* 2004; 29: 639-643).

Without wishing being bound by theory or mechanism, Imiquimod appears to act via TLR-7 (Hemmi et al. "Small anti-viral compounds activate immune cells via the TLR 7 MyD88-dependent signaling pathway". *Nat. Immunol* 2002; 3:196-200). Imiquimod can inhibit the progression of actinic keratosis (AK) into invasive skin cancer, usually squamous cell carcinoma (SCC). Although imiquimod does not appear to have direct antineoplastic activity (Schon et al. "Tumor-selective induction of apoptosis and the small-molecule immune response modifier imiquimod." *J Natl. Cancer inst.* 2003, 95:1138-49), it has shown efficacy against a variety of tumors, including skin tumors.

As used herein the term "retinoid agent" refers to compounds having the general structure of vitamin A (retinol) and variations of that structure having a similar biological and pharmacological activity as retinol. Examples of retinoids include, but are not limited to, retinol, retinal, retinyl acetate, retinaldehyde, retinyl palmitate, retinoic acid, retinyl propionate, retinyl linoleate, dehydroretinol, eretinate, eretrin, motretinide, tazarotene, isotretinoin, tretinoin, adapalene, bexarotene, fenretinide, and alitretinoin.

As will be recognized by one of ordinary skill in the art upon study of the present document, in some cases it could be desirable to include further ingredients in the composition as described herein. Examples of such further ingredients include, but are not limited to salicylic acid, urea, alpha-hydroxy acids, and beta-hydroxy acids. Those of ordinary skill in the art will immediately recognize that various additional ingredients can be beneficial to provide in certain embodiments of the claimed composition, e.g., vehicle enhancers such as propylene glycol.

Compositions of the presently-disclosed subject matter are useful for the treatment of various conditions affecting skin and mucosal surfaces (mouth and genetalia) of a subject. Such conditions include a wart, molluscum contagiosum, a keloid, and a skin cancer.

The term "wart" as used herein refers to a growth caused by a papillomavirus at any location on a subject, and is inclusive of, but not limited to, warts caused by human papollomaviruses (HPV), such as, verruca vulgaris (common wart), verruca plana (flat wart) condyloma acuminatum or verruca acuminate (genital wart), and verruca pedis (plantar wart).

Molluscum contagiosum is an infection caused by a group of viruses in the Pox-viridae family, known as mulluscum contagiosum viruses (MCV).

The term "keloid" as used herein is inclusive of a keloid scar resulting from an overgrowth of scar tissue that occurs at the site of a skin injury. Although the term keloid is used to refer to refer an overgrowth of a scar having a tendency to migrate beyond the boundaries of the original skin injury, and hypertrophic scar is a term used to refer to raised scars that do not so-migrate, as used herein, the term "keloid" is inclusive of both keloid scars and hypertrophic scars, both of which are characterized by an overgrowth of scar tissue, which can be accompanied by itching and pain.

As used herein, the term "skin cancer" is used to refer to malignant and premalignant skin cancers. As such, the term "skin cancer" is inclusive of melanoma and non-melanoma skin cancers, actinic keratoses, basal cell carcinomas, squamous cell carcinoma-in-situ or Bowen's disease, melanoma in-situ, and other unresectable carcinomas. The term "skin cancer" refers to both primary and secondary cancers of the skin. In this regard, the term is inclusive of metastatic lesions caused by a primary skin cancer or another cancer that metastasizes to the skin. Further, the term includes the following nonlimiting examples: cutaneous T-cell lymphoma, extramammary Paget's disease, lentigo maligna, cutaneous melanoma metastases, and cutaneous leishmaniasis. See Jackson and Callen, (In Press) Chapter 128: Immunomodulators. In Bolognia, Jorizzo, and Rapini *Dermatology*, 3d. Edition, which is incorporated herein by this reference.

As used herein, the terms "treatment" or "treating" relate to any treatment of a condition affecting the skin and/or mucosal surface of a subject, including but not limited to prophylactic treatment and therapeutic treatment As such, the terms treatment or treating include, but are not limited to: inhibiting the progression of a condition; arresting or inhibiting the development of a condition; reducing the severity of a condition; ameliorating or relieving symptoms associated with a condition; and causing a regression of the condition or one or more of the symptoms associated with the condition. For example, treatment or treating can include, but are not limited to: reduction in size and in thickness and hyperkeratinization; reduced pain; reduced itching; reduced inflammation adjacent to, but not the actual treatment area (redness and swelling away from the zone of topical application); reduction in the number of lesions; reduction in the occurrence of new lesions, resolution of lesions beyond the treated area ("field effect"), and reduction in rates of remission, e.g., due to increased immune surveillance.

As used herein, the term "effective amount" refers to a dosage sufficient to provide treatment for the condition being treated. This can vary depending on the patient, the condition and the treatment being effected. The exact amount that is required will vary from subject to subject, depending on the species, age, and general condition of the subject, the particular carrier or adjuvant being used, mode of administration, and the like. As such, the effective amount will vary based on the particular circumstances, and an appropriate effective amount can be determined in a particular case by one of ordinary skill in the art using only routine experimentation.

As used herein, the term "subject" includes both human and animal subjects. Thus, veterinary therapeutic uses are provided in accordance with the presently disclosed subject matter. As such, the presently disclosed subject matter provides for the treatment of mammals such as humans and non-human primates, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, camels, and horses. The term does not denote a particular age or sex. Thus, adult and newborn subjects, as well as fetuses, whether male or female, are intended to be covered.

Contemplated subjects include transplant patients, who can be at risk for developing a cancer, particularly after extended use of antirejection therapy. Such subjects can develop squamous cell carcinomas, for example, which tend to be more aggressive and which are a significant cause of death in these subjects. Compositions and methods of the presently-disclosed subject matter can be used for chemoprevention in such a transplant patient.

As proposed herein, including an imidazoquinoline compound and a retinoid agent in the same composition increases the efficacy of the components of the composition, as compared their efficacy when administered separately. In some embodiments, the increase in the efficacy is more than an additive effect, and combination of the imidazoquinoline compound and the retinoid agent can be described as having a synergistic effect.

As used herein, "synergy" and "synergistic effect" can refer to any substantial enhancement, in a composition of at least two compounds, of a measurable effect when compared with the effect of a component of the composition, e.g., one active compound alone. Measurable effects could include, for example, reduction in thickness and hyperkeratinization, reduced pain, inflammation adjacent to, but not the actual treatment area (redness and swelling away from the zone of topical application), fewer or reduction of new lesions demonstrating the immune recognition rather than simply local irritation, and resolution of verrucae beyond the treated area demonstrating a systemic recognition or "field effect"

Synergy is a specific feature of a blend of compounds, and is above any background level of enhancement that would be due solely to, e.g., additive effects of any random combination of ingredients. This combination has demonstrated clinically synergistic effects.

In some embodiments, a substantial enhancement of a measurable effect can be expressed as a coefficient of synergy. A coefficient of synergy is an expression of a comparison between measured effects of a composition and measured effects of a comparison composition. The comparison composition can be a component of the composition, e.g., imiquimod. In some embodiments, the synergy coefficient can be adjusted for differences in concentration of the complete composition and the comparison composition.

Synergy coefficients can be calculated as follows. An activity ratio (R) can be calculated by dividing the % effect of the composition (AB) by the % effect of the comparison compound ($X_n$), as follows:

$$R=AB/X_n. \qquad \text{Formula 1}$$

A concentration adjustment factor (F) can be calculated based on the concentration ($C_n$), i.e., % (wt/wt) or % (vol/vol), of the comparison compound in the composition, as follows:

$$F=100/C_n \qquad \text{Formula 2}$$

The synergy coefficient (S) can then be calculated by multiplying the activity ratio (R) and the concentration adjustment factor (F), as follows:

$$S=(R)(F) \qquad \text{Formula 3}$$

As such, the synergy coefficient (S) can also by calculated, as follows:

$$S=[(AB/X_n)(100)]/C_n \qquad \text{Formula 4}$$

In Formula 4, AB is expressed as % effect of the blend, $X_n$ is expressed as % effect of the comparison compound ($X_n$), and $C_n$ is expressed as % (wt/wt) or % (vol/vol) concentration of the comparison composition in the blend. Additional information related to calculating synergy coefficients can be found in the Examples set forth in this document.

In some embodiments, a coefficient of synergy of about 1.1, 1.2, 1.3, 1.4, or 1.5 can be substantial and commercially desirable. In other embodiments, the coefficient of synergy can be from about 1.6 to about 5, including but not limited to about 1.8, 2.0, 2.5, 3.0, 3.5, 4.0, and 4.5. In other embodiments, the coefficient of synergy can be from about 5 to 50, including but not limited to about 10, 15, 20, 25, 30, 35, 40, and 45. In other embodiments, the coefficient of synergy can be from about 50 to about 500, or more, including but not limited to about 50, 75, 100, 125, 150, 200, 250, 300, 350, 400, and 450. Any coefficient of synergy above 500, 1000, or 5000 is also contemplated within embodiments of the compositions.

Given that a broad range of synergies can be found in various embodiments of the invention, it is expressly noted that a coefficient of synergy can be described as being "greater than" a given number and therefore not necessarily limited to being within the bounds of a range having a lower and an upper numerical limit. Likewise, in some embodiments of the invention, certain low synergy coefficients, or lower ends of ranges, are expressly excluded. Accordingly, in some embodiments, synergy can be expressed as being "greater than" a given number that constitutes a lower limit of synergy for such an embodiment. For example, in some embodiments, the synergy coefficient is equal to or greater than 25; in such an embodiment, all synergy coefficients below 25, even though substantial, are expressly excluded.

In some embodiments, synergy or synergistic effect associated with a composition can be determined using calculations similar to those described in Colby, S. R., "Calculating synergistic and antagonistic responses of herbicide combinations," Weeds (1967) 15:1, pp. 20-22, which is incorporated herein by this reference. In this regard, the following formula can be used to express an expected % effect (E) of a composition including two compounds, Compound X and Compound Y:

$$E=X+Y-(X*Y/100) \qquad \text{Formula 5}$$

In Formula 5, X is the measured actual % effect of Compound X in the composition, and Y is the measured actual % effect of Compound Y of the composition. The expected % effect (E) of the composition is then compared to a measured actual % effect (A) of the composition. If the actual % effect (A) that is measured differs from the expected % effect (E) as calculated by the formula, then the difference is due to an interaction of the compounds. Thus, the composition has synergy (a positive interaction of the compounds) when A>E. Further, there is a negative interaction (antagonism) when A<E.

As noted herein, and as known to those of ordinary skill in the art, imidazoquinoline compounds have notorious solubility challenges, calling into question the ability to provide a compatible and stable composition including both an imidazoquinoline compound and a retinoid agent. Despite such challenges, the present inventor contemplated the composition and it was surprisingly discovered that an imidazoquinoline compound and a retinoid agent could be formulated in a single composition with unexpectedly beneficial properties (See the Examples for further details). Such beneficial properties include physical stability and chemical stability of the composition.

Stability is a specific feature of embodiments of the composition of the presently-disclosed subject matter. In some embodiments, the composition is substantially stable at a temperature up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55° C. for a period of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 days. In some embodiments, the composition is substantially stable at a temperature of 50° C. for a period of four (4) weeks. In some embodiments, the composition is substantially stable at a temperature of 40° C. for a period of four (4) weeks. In some embodiments, the composition is substantially stable at a temperature of 25° C. for a period of four (4) weeks. In some embodiments, the composition is substantially stable following up to three freeze/warm cycles from −20° C. to 40° C. As used herein, the term "substantially stable" can refer to physical and/or chemical stability. As will be recognized by those of ordinary skill in the art, the term "substantially stable" can refer to stability of the composition under certain conditions, relative to an initial composition (i.e., when a particular batch of the composition is initially prepared). In this regard, as will be recognized by those of ordinary skill in the art, one manner in which stability of a particular embodiment of the composition can be determined is as follows: preparing a batch of the embodiment of the composition, making an initial assessment of a sample of the composition (control sample), subjecting a sample of the composition to conditions of interest (e.g., storage at a particular temperature for a particular time period) (test sample), making an assessment of the test sample, and comparing the assessment of the control sample to the assessment of the test sample. In some cases, to assess stability, it can be desirable to measure and compare the amount of the imidazoquinoline compound and the amount of the retinoid agent in the control sample and in the test same. Calculations can be made to determine whether the amounts present in the test sample are 100%±20, 19, 18, 17, 16, 15, 14, 13, 12, 11, 10, 9, 8, 7, 6, 5, 4, 3, 2, 1, 0.5, or 0.1% of the amount that is in the control sample.

In some embodiments, a composition is provided wherein the imidazoquinoline compound and the retinoid agent are provided in a particular ratio relative to one another. For example, in some embodiments the imiquimod and the retinoid agent are provided in a ratio of about 20:1 to about 1:20, wherein the ratio is a weight ratio. In some embodiments the imiquimod and the retinoid agent are provided in a ratio of about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20.

In some embodiments, the imidazoquinoline compound is provided in the composition at a final concentration of between about 10% (wt/wt) and about 0.1% (wt/wt). In some embodiments, imidazoquinoline compound is provided at a final concentration of between about 7% and about 3% (wt/wt). In some embodiments, the imidazoquinoline compound is provided at a final concentration of about 10.00%, 9.99%, 9.98%, 9.97%, 9.96%, 9.95%, 9.94%, 9.93%, 9.92%, 9.91%, 9.90%, 9.89%, 9.88%, 9.87%, 9.86%, 9.85%, 9.84%, 9.83%, 9.82%, 9.81%, 9.80%, 9.79%, 9.78%, 9.77%, 9.76%, 9.75%, 9.74%, 9.73%, 9.72%, 9.71%, 9.70%, 9.69%, 9.68%, 9.67%, 9.66%, 9.65%, 9.64%, 9.63%, 9.62%, 9.61%, 9.60%, 9.59%, 9.58%, 9.57%, 9.56%, 9.55%, 9.54%, 9.53%, 9.52%, 9.51%, 9.50%, 9.49%, 9.48%, 9.47%, 9.46%, 9.45%, 9.44%, 9.43%, 9.42%, 9.41%, 9.40%, 9.39%, 9.38%, 9.37%, 9.36%, 9.35%, 9.34%, 9.33%, 9.32%, 9.31%, 9.30%, 9.29%, 9.28%, 9.27%, 9.26%, 9.25%, 9.24%, 9.23%, 9.22%, 9.21%, 9.20%, 9.19%, 9.18%, 9.17%, 9.16%, 9.15%, 9.14%, 9.13%, 9.12%, 9.11%, 9.10%, 9.09%, 9.08%, 9.07%, 9.06%, 9.05%, 9.04%, 9.03%, 9.02%, 9.01%, 9.00%, 8.99%, 8.98%, 8.97%, 8.96%, 8.95%, 8.94%, 8.93%, 8.92%, 8.91%, 8.90%, 8.89%, 8.88%, 8.87%, 8.86%, 8.85%, 8.84%, 8.83%, 8.82%, 8.81%, 8.80%, 8.79%, 8.78%, 8.77%, 8.76%, 8.75%, 8.74%, 8.73%, 8.72%, 8.71%, 8.70%, 8.69%, 8.68%, 8.67%, 8.66%, 8.65%, 8.64%, 8.63%, 8.62%, 8.61%, 8.60%, 8.59%, 8.58%, 8.57%, 8.56%, 8.55%, 8.54%, 8.53%, 8.52%, 8.51%, 8.50%, 8.49%, 8.48%, 8.47%, 8.46%, 8.45%, 8.44%, 8.43%, 8.42%, 8.41%, 8.40%, 8.39%, 8.38%, 8.37%, 8.36%, 8.35%, 8.34%, 8.33%, 8.32%, 8.31%, 8.30%, 8.29%, 8.28%, 8.27%, 8.26%, 8.25%, 8.24%, 8.23%, 8.22%, 8.21%, 8.20%, 8.19%, 8.18%, 8.17%, 8.16%, 8.15%, 8.14%, 8.13%, 8.12%, 8.11%, 8.10%, 8.09%, 8.08%, 8.07%, 8.06%, 8.05%, 8.04%, 8.03%, 8.02%, 8.01%, 8.00%, 7.99%, 7.98%, 7.97%, 7.96%, 7.95%, 7.94%, 7.93%, 7.92%, 7.91%, 7.90%, 7.89%, 7.88%, 7.87%, 7.86%, 7.85%, 7.84%, 7.83%, 7.82%, 7.81%, 7.80%, 7.79%, 7.78%, 7.77%, 7.76%, 7.75%, 7.74%, 7.73%, 7.72%, 7.71%, 7.70%, 7.69%, 7.68%, 7.67%, 7.66%, 7.65%, 7.64%, 7.63%, 7.62%, 7.61%, 7.60%, 7.59%, 7.58%, 7.57%, 7.56%, 7.55%, 7.54%, 7.53%, 7.52%, 7.51%, 7.50%, 7.49%, 7.48%, 7.47%, 7.46%, 7.45%, 7.44%, 7.43%, 7.42%, 7.41%, 7.40%, 7.39%, 7.38%, 7.37%, 7.36%, 7.35%, 7.34%, 7.33%, 7.32%, 7.31%, 7.30%, 7.29%, 7.28%, 7.27%, 7.26%, 7.25%, 7.24%, 7.23%, 7.22%, 7.21%, 7.20%, 7.19%, 7.18%, 7.17%, 7.16%, 7.15%, 7.14%, 7.13%, 7.12%, 7.11%, 7.10%, 7.09%, 7.08%, 7.07%, 7.06%, 7.05%, 7.04%, 7.03%, 7.02%, 7.01%, 7.00%, 6.99%, 6.98%, 6.97%, 6.96%, 6.95%, 6.94%, 6.93%, 6.92%, 6.91%, 6.90%, 6.89%, 6.88%, 6.87%, 6.86%, 6.85%, 6.84%, 6.83%, 6.82%, 6.81%, 6.80%, 6.79%, 6.78%, 6.77%, 6.76%, 6.75%, 6.74%, 6.73%, 6.72%, 6.71%, 6.70%, 6.69%, 6.68%, 6.67%, 6.66%, 6.65%, 6.64%, 6.63%, 6.62%, 6.61%, 6.60%, 6.59%, 6.58%, 6.57%, 6.56%, 6.55%, 6.54%, 6.53%, 6.52%, 6.51%, 6.50%, 6.49%, 6.48%, 6.47%, 6.46%, 6.45%, 6.44%, 6.43%, 6.42%, 6.41%, 6.40%, 6.39%, 6.38%, 6.37%, 6.36%, 6.35%, 6.34%, 6.33%, 6.32%, 6.31%, 6.30%, 6.29%, 6.28%, 6.27%, 6.26%, 6.25%, 6.24%, 6.23%, 6.22%, 6.21%, 6.20%, 6.19%, 6.18%, 6.17%, 6.16%, 6.15%, 6.14%, 6.13%, 6.12%, 6.11%, 6.10%, 6.09%, 6.08%, 6.07%, 6.06%, 6.05%, 6.04%, 6.03%, 6.02%, 6.01%, 6.00%, 5.99%, 5.98%, 5.97%, 5.96%, 5.95%, 5.94%, 5.93%, 5.92%, 5.91%, 5.90%, 5.89%, 5.88%, 5.87%, 5.86%, 5.85%, 5.84%, 5.83%, 5.82%, 5.81%, 5.80%, 5.79%, 5.78%, 5.77%, 5.76%, 5.75%, 5.74%, 5.73%, 5.72%, 5.71%, 5.70%, 5.69%, 5.68%, 5.67%, 5.66%, 5.65%, 5.64%, 5.63%, 5.62%, 5.61%, 5.60%, 5.59%, 5.58%, 5.57%, 5.56%, 5.55%, 5.54%, 5.53%, 5.52%, 5.51%, 5.50%, 5.49%, 5.48%, 5.47%, 5.46%, 5.45%, 5.44%, 5.43%, 5.42%, 5.41%, 5.40%, 5.39%, 5.38%, 5.37%, 5.36%, 5.35%, 5.34%, 5.33%, 5.32%, 5.31%, 5.30%, 5.29%, 5.28%, 5.27%, 5.26%, 5.25%, 5.24%, 5.23%, 5.22%, 5.21%, 5.20%, 5.19%, 5.18%, 5.17%, 5.16%, 5.15%, 5.14%, 5.13%, 5.12%, 5.11%, 5.10%, 5.09%, 5.08%, 5.07%, 5.06%, 5.05%, 5.04%, 5.03%, 5.02%, 5.01%, 5.00%, 4.99%, 4.98%, 4.97%, 4.96%, 4.95%, 4.94%, 4.93%, 4.92%, 4.91%, 4.90%, 4.89%, 4.88%, 4.87%, 4.86%, 4.85%, 4.84%, 4.83%, 4.82%, 4.81%, 4.80%, 4.79%, 4.78%, 4.77%, 4.76%, 4.75%, 4.74%, 4.73%, 4.72%, 4.71%, 4.70%, 4.69%, 4.68%, 4.67%, 4.66%, 4.65%, 4.64%, 4.63%, 4.62%, 4.61%, 4.60%, 4.59%, 4.58%, 4.57%, 4.56%, 4.55%, 4.54%, 4.53%, 4.52%, 4.51%, 4.50%, 4.49%, 4.48%, 4.47%, 4.46%, 4.45%, 4.44%, 4.43%, 4.42%, 4.41%, 4.40%, 4.39%, 4.38%, 4.37%, 4.36%, 4.35%, 4.34%, 4.33%, 4.32%, 4.31%, 4.30%, 4.29%, 4.28%, 4.27%, 4.26%, 4.25%, 4.24%, 4.23%, 4.22%, 4.21%, 4.20%, 4.19%, 4.18%, 4.17%, 4.16%, 4.15%, 4.14%, 4.13%, 4.12%, 4.11%, 4.10%, 4.09%, 4.08%, 4.07%, 4.06%, 4.05%, 4.04%, 4.03%, 4.02%, 4.01%, 4.00%, 3.99%, 3.98%, 3.97%, 3.96%, 3.95%, 3.94%, 3.93%, 3.92%, 3.91%, 3.90%, 3.89%, 3.88%, 3.87%, 3.86%, 3.85%, 3.84%, 3.83%, 3.82%, 3.81%, 3.80%, 3.79%, 3.78%, 3.77%, 3.76%, 3.75%, 3.74%, 3.73%, 3.72%, 3.71%, 3.70%, 3.69%, 3.68%, 3.67%, 3.66%, 3.65%, 3.64%, 3.63%, 3.62%, 3.61%, 3.60%, 3.59%, 3.58%, 3.57%, 3.56%, 3.55%, 3.54%, 3.53%, 3.52%, 3.51%, 3.50%, 3.49%, 3.48%, 3.47%, 3.46%, 3.45%, 3.44%, 3.43%, 3.42%, 3.41%, 3.40%, 3.39%, 3.38%, 3.37%, 3.36%, 3.35%, 3.34%, 3.33%, 3.32%, 3.31%, 3.30%, 3.29%, 3.28%, 3.27%, 3.26%, 3.25%, 3.24%, 3.23%, 3.22%, 3.21%, 3.20%, 3.19%, 3.18%, 3.17%, 3.16%, 3.15%, 3.14%, 3.13%, 3.12%, 3.11%, 3.10%, 3.09%, 3.08%, 3.07%, 3.06%, 3.05%, 3.04%, 3.03%, 3.02%, 3.01%, 3.00%, 2.99%, 2.98%, 2.97%, 2.96%, 2.95%, 2.94%, 2.93%, 2.92%, 2.91%, 2.90%, 2.89%, 2.88%, 2.87%, 2.86%, 2.85%, 2.84%, 2.83%, 2.82%, 2.81%, 2.80%, 2.79%, 2.78%, 2.77%, 2.76%, 2.75%, 2.74%, 2.73%, 2.72%, 2.71%, 2.70%, 2.69%, 2.68%, 2.67%, 2.66%, 2.65%, 2.64%, 2.63%, 2.62%, 2.61%, 2.60%, 2.59%, 2.58%, 2.57%, 2.56%, 2.55%, 2.54%, 2.53%, 2.52%, 2.51%, 2.50%, 2.49%, 2.48%, 2.47%, 2.46%, 2.45%, 2.44%, 2.43%, 2.42%, 2.41%, 2.40%, 2.39%, 2.38%, 2.37%, 2.36%, 2.35%, 2.34%, 2.33%, 2.32%, 2.31%, 2.30%, 2.29%, 2.28%, 2.27%, 2.26%, 2.25%, 2.24%, 2.23%, 2.22%, 2.21%, 2.20%, 2.19%, 2.18%, 2.17%, 2.16%, 2.15%, 2.14%, 2.13%, 2.12%, 2.11%, 2.10%, 2.09%, 2.08%, 2.07%, 2.06%, 2.05%, 2.04%, 2.03%, 2.02%, 2.01%, 2.00%, 1.99%, 1.98%, 1.97%, 1.96%, 1.95%, 1.94%, 1.93%, 1.92%, 1.91%, 1.90%, 1.89%, 1.88%, 1.87%, 1.86%, 1.85%, 1.84%, 1.83%, 1.82%, 1.81%, 1.80%, 1.79%, 1.78%, 1.77%, 1.76%, 1.75%, 1.74%, 1.73%, 1.72%, 1.71%, 1.70%, 1.69%, 1.68%, 1.67%, 1.66%, 1.65%, 1.64%, 1.63%, 1.62%, 1.61%, 1.60%, 1.59%, 1.58%, 1.57%, 1.56%, 1.55%, 1.54%, 1.53%, 1.52%, 1.51%, 1.50%, 1.49%, 1.48%, 1.47%, 1.46%, 1.45%, 1.44%, 1.43%, 1.42%, 1.41%, 1.40%, 1.39%, 1.38%, 1.37%, 1.36%, 1.35%, 1.34%, 1.33%, 1.32%, 1.31%, 1.30%, 1.29%, 1.28%, 1.27%, 1.26%, 1.25%, 1.24%, 1.23%, 1.22%, 1.21%, 1.20%, 1.19%, 1.18%, 1.17%, 1.16%, 1.15%, 1.14%, 1.13%, 1.12%, 1.11%, 1.10%, 1.09%, 1.08%, 1.07%, 1.06%, 1.05%, 1.04%, 1.03%, 1.02%, 1.01%, 1.00%, 0.99%, 0.98%, 0.97%, 0.96%, 0.95%, 0.94%, 0.93%, 0.92%, 0.91%, 0.90%, 0.89%, 0.88%, 0.87%, 0.86%, 0.85%, 0.84%, 0.83%, 0.82%, 0.81%, 0.80%, 0.79%, 0.78%, 0.77%, 0.76%, 0.75%, 0.74%, 0.73%, 0.72%, 0.71%, 0.70%, 0.69%, 0.68%, 0.67%, 0.66%, 0.65%, 0.64%, 0.63%, 0.62%, 0.61%, 0.60%, 0.59%, 0.58%, 0.57%, 0.56%, 0.55%, 0.54%, 0.53%, 0.52%, 0.51%, 0.50%, 0.49%, 0.48%, 0.47%, 0.46%, 0.45%, 0.44%, 0.43%, 0.42%, 0.41%, 0.40%, 0.39%, 0.38%, 0.37%, 0.36%, 0.35%, 0.34%, 0.33%, 0.32%, 0.31%, 0.30%, 0.29%, 0.28%, 0.27%, 0.26%, 0.25%, 0.24%, 0.23%, 0.22%, 0.21%, 0.20%, 0.19%, 0.18%, 0.17%, 0.16%, 0.15%, 0.14%, 0.13%, 0.12%, 0.11%, or 0.10% (wt/wt). In some embodiments, the imidazoquinoline compound is provided at a final concentration as recited in this paragraph, and is selected from imiquimod, resiquimod, and sotirimod. In some embodiments, the imidazoquinoline compound is imiquimod, which provided at a final concentration as recited in this paragraph. In some embodiments, the imidazoquinoline compound is resiquimod, which provided at a final concentration as recited in this paragraph. In some embodiments, the imidazoquinoline compound is sotirimod, which provided at a final concentration as recited in this paragraph.

In some embodiments, the retinoid agent is provided in the composition at a final concentration between about 1% (wt/wt) and about 0.001% (wt/wt). In some embodiments, the retinoid agent is provided at a final concentration between about 1% (wt/wt) and about 0.025% (wt/wt). In some embodiments, the retinoid agent is provided at a concentration between about 0.5% (wt/wt) and about 0.01% (wt/wt). In some embodiments, the retinoid agent is provided at a final concentration of about 1.000%, 0.999%, 0.998%, 0.997%, 0.996%, 0.995%, 0.994%, 0.993%, 0.992%, 0.991%, 0.990%, 0.989%, 0.988%, 0.987%, 0.986%, 0.985%, 0.984%, 0.983%, 0.982%, 0.981%, 0.980%, 0.979%, 0.978%, 0.977%, 0.976%, 0.975%, 0.974%, 0.973%, 0.972%, 0.971%, 0.970%, 0.969%, 0.968%, 0.967%, 0.966%, 0.965%, 0.964%, 0.963%, 0.962%, 0.961%, 0.960%, 0.959%, 0.958%, 0.957%, 0.956%, 0.955%, 0.954%, 0.953%, 0.952%, 0.951%, 0.950%, 0.949%, 0.948%, 0.947%, 0.946%, 0.945%, 0.944%, 0.943%, 0.942%, 0.941%, 0.940%, 0.939%, 0.938%, 0.937%, 0.936%, 0.935%, 0.934%, 0.933%, 0.932%, 0.931%, 0.930%, 0.929%, 0.928%, 0.927%, 0.926%, 0.925%, 0.924%, 0.923%, 0.922%, 0.921%, 0.920%, 0.919%, 0.918%, 0.917%, 0.916%, 0.915%, 0.914%, 0.913%, 0.912%, 0.911%, 0.910%, 0.909%, 0.908%, 0.907%, 0.906%, 0.905%, 0.904%, 0.903%, 0.902%, 0.901%, 0.900%, 0.899%, 0.898%, 0.897%, 0.896%, 0.895%, 0.894%, 0.893%, 0.892%, 0.891%, 0.890%, 0.889%, 0.888%, 0.887%, 0.886%, 0.885%, 0.884%, 0.883%, 0.882%, 0.881%, 0.880%, 0.879%, 0.878%, 0.877%, 0.876%, 0.875%, 0.874%, 0.873%, 0.872%, 0.871%, 0.870%, 0.869%, 0.868%, 0.867%, 0.866%, 0.865%, 0.864%, 0.863%, 0.862%, 0.861%, 0.860%, 0.859%, 0.858%, 0.857%, 0.856%, 0.855%, 0.854%, 0.853%, 0.852%, 0.851%, 0.850%, 0.849%, 0.848%, 0.847%, 0.846%, 0.845%, 0.844%, 0.843%, 0.842%, 0.841%, 0.840%, 0.839%, 0.838%, 0.837%, 0.836%, 0.835%, 0.834%, 0.833%, 0.832%, 0.831%, 0.830%, 0.829%, 0.828%, 0.827%, 0.826%, 0.825%, 0.824%, 0.823%, 0.822%, 0.821%, 0.820%, 0.819%, 0.818%, 0.817%, 0.816%, 0.815%, 0.814%, 0.813%, 0.812%, 0.811%, 0.810%, 0.809%, 0.808%, 0.807%, 0.806%, 0.805%, 0.804%, 0.803%, 0.802%, 0.801%, 0.800%, 0.799%, 0.798%, 0.797%, 0.796%, 0.795%, 0.794%, 0.793%, 0.792%, 0.791%, 0.790%, 0.789%, 0.788%, 0.787%, 0.786%, 0.785%, 0.784%, 0.783%, 0.782%, 0.781%, 0.780%, 0.779%, 0.778%, 0.777%, 0.776%, 0.775%, 0.774%, 0.773%, 0.772%, 0.771%, 0.770%, 0.769%, 0.768%, 0.767%, 0.766%, 0.765%, 0.764%, 0.763%, 0.762%, 0.761%, 0.760%, 0.759%, 0.758%, 0.757%, 0.756%, 0.755%, 0.754%, 0.753%, 0.752%, 0.751%, 0.750%, 0.749%, 0.748%, 0.747%, 0.746%, 0.745%, 0.744%, 0.743%, 0.742%, 0.741%, 0.740%, 0.739%, 0.738%, 0.737%, 0.736%, 0.735%, 0.734%, 0.733%, 0.732%, 0.731%, 0.730%, 0.729%, 0.728%, 0.727%, 0.726%, 0.725%, 0.724%, 0.723%, 0.722%, 0.721%, 0.720%, 0.719%, 0.718%, 0.717%, 0.716%, 0.715%, 0.714%, 0.713%, 0.712%, 0.711%, 0.710%, 0.709%, 0.708%, 0.707%, 0.706%, 0.705%, 0.704%, 0.703%, 0.702%, 0.701%, 0.700%, 0.699%, 0.698%, 0.697%, 0.696%, 0.695%, 0.694%, 0.693%, 0.692%, 0.691%, 0.690%, 0.689%, 0.688%, 0.687%, 0.686%, 0.685%, 0.684%, 0.683%, 0.682%, 0.681%, 0.680%, 0.679%, 0.678%, 0.677%, 0.676%, 0.675%, 0.674%, 0.673%, 0.672%, 0.671%, 0.670%, 0.669%, 0.668%, 0.667%, 0.666%, 0.665%, 0.664%, 0.663%, 0.662%, 0.661%, 0.660%, 0.659%, 0.658%, 0.657%, 0.656%, 0.655%, 0.654%, 0.653%, 0.652%, 0.651%, 0.650%, 0.649%, 0.648%, 0.647%, 0.646%, 0.645%, 0.644%, 0.643%, 0.642%, 0.641%, 0.640%, 0.639%, 0.638%, 0.637%, 0.636%, 0.635%, 0.634%, 0.633%, 0.632%, 0.631%, 0.630%, 0.629%, 0.628%, 0.627%, 0.626%, 0.625%, 0.624%, 0.623%, 0.622%, 0.621%, 0.620%, 0.619%, 0.618%, 0.617%, 0.616%, 0.615%, 0.614%, 0.613%, 0.612%, 0.611%, 0.610%, 0.609%, 0.608%, 0.607%, 0.606%, 0.605%, 0.604%, 0.603%, 0.602%, 0.601%, 0.600%, 0.599%, 0.598%, 0.597%, 0.596%, 0.595%, 0.594%, 0.593%, 0.592%, 0.591%, 0.590%, 0.589%, 0.588%, 0.587%, 0.586%, 0.585%, 0.584%, 0.583%, 0.582%, 0.581%, 0.580%, 0.579%, 0.578%, 0.577%, 0.576%, 0.575%, 0.574%, 0.573%, 0.572%, 0.571%, 0.570%, 0.569%, 0.568%, 0.567%, 0.566%, 0.565%, 0.564%, 0.563%, 0.562%, 0.561%, 0.560%, 0.559%, 0.558%, 0.557%, 0.556%, 0.555%, 0.554%, 0.553%, 0.552%, 0.551%, 0.550%, 0.549%, 0.548%, 0.547%, 0.546%, 0.545%, 0.544%, 0.543%, 0.542%, 0.541%, 0.540%, 0.539%, 0.538%, 0.537%, 0.536%, 0.535%, 0.534%, 0.533%, 0.532%, 0.531%, 0.530%, 0.529%, 0.528%, 0.527%, 0.526%, 0.525%, 0.524%, 0.523%, 0.522%, 0.521%, 0.520%, 0.519%, 0.518%, 0.517%, 0.516%, 0.515%, 0.514%, 0.513%, 0.512%, 0.511%, 0.510%, 0.509%, 0.508%, 0.507%, 0.506%, 0.505%, 0.504%, 0.503%, 0.502%, 0.501%, 0.500%, 0.499%, 0.498%, 0.497%, 0.496%, 0.495%, 0.494%, 0.493%, 0.492%, 0.491%, 0.490%, 0.489%, 0.488%, 0.487%, 0.486%, 0.485%, 0.484%, 0.483%, 0.482%, 0.481%, 0.480%, 0.479%, 0.478%, 0.477%, 0.476%, 0.475%, 0.474%, 0.473%, 0.472%, 0.471%, 0.470%, 0.469%, 0.468%, 0.467%, 0.466%, 0.465%, 0.464%, 0.463%, 0.462%, 0.461%, 0.460%, 0.459%, 0.458%, 0.457%, 0.456%, 0.455%, 0.454%, 0.453%, 0.452%, 0.451%, 0.450%, 0.449%, 0.448%, 0.447%, 0.446%, 0.445%, 0.444%, 0.443%, 0.442%, 0.441%, 0.440%, 0.439%, 0.438%, 0.437%, 0.436%, 0.435%, 0.434%, 0.433%, 0.432%, 0.431%, 0.430%, 0.429%, 0.428%, 0.427%, 0.426%, 0.425%, 0.424%, 0.423%, 0.422%, 0.421%, 0.420%, 0.419%, 0.418%, 0.417%, 0.416%, 0.415%, 0.414%, 0.413%, 0.412%, 0.411%, 0.410%, 0.409%, 0.408%, 0.407%, 0.406%, 0.405%, 0.404%, 0.403%, 0.402%, 0.401%, 0.400%, 0.399%, 0.398%, 0.397%, 0.396%, 0.395%, 0.394%, 0.393%, 0.392%, 0.391%, 0.390%, 0.389%, 0.388%, 0.387%, 0.386%, 0.385%, 0.384%, 0.383%, 0.382%, 0.381%, 0.380%, 0.379%, 0.378%, 0.377%, 0.376%, 0.375%, 0.374%, 0.373%, 0.372%, 0.371%, 0.370%, 0.369%, 0.368%, 0.367%, 0.366%, 0.365%, 0.364%, 0.363%, 0.362%, 0.361%, 0.360%, 0.359%, 0.358%, 0.357%, 0.356%, 0.355%, 0.354%, 0.353%, 0.352%, 0.351%, 0.350%, 0.349%, 0.348%, 0.347%, 0.346%, 0.345%, 0.344%, 0.343%, 0.342%, 0.341%, 0.340%, 0.339%, 0.338%, 0.337%, 0.336%, 0.335%, 0.334%, 0.333%, 0.332%, 0.331%, 0.330%, 0.329%, 0.328%, 0.327%, 0.326%, 0.325%, 0.324%, 0.323%, 0.322%, 0.321%, 0.320%, 0.319%, 0.318%, 0.317%, 0.316%, 0.315%, 0.314%, 0.313%, 0.312%, 0.311%, 0.310%, 0.309%, 0.308%, 0.307%, 0.306%, 0.305%, 0.304%, 0.303%, 0.302%, 0.301%, 0.300%, 0.299%, 0.298%, 0.297%, 0.296%, 0.295%, 0.294%, 0.293%, 0.292%, 0.291%, 0.290%, 0.289%, 0.288%, 0.287%, 0.286%, 0.285%, 0.284%, 0.283%, 0.282%, 0.281%, 0.280%, 0.279%, 0.278%, 0.277%, 0.276%, 0.275%, 0.274%, 0.273%, 0.272%, 0.271%, 0.270%, 0.269%, 0.268%, 0.267%, 0.266%, 0.265%, 0.264%, 0.263%, 0.262%, 0.261%, 0.260%, 0.259%, 0.258%, 0.257%, 0.256%, 0.255%, 0.254%, 0.253%, 0.252%, 0.251%, 0.250%, 0.249%, 0.248%, 0.247%, 0.246%, 0.245%, 0.244%, 0.243%, 0.242%, 0.241%, 0.240%, 0.239%, 0.238%, 0.237%, 0.236%, 0.235%, 0.234%, 0.233%, 0.232%, 0.231%, 0.230%, 0.229%, 0.228%, 0.227%, 0.226%, 0.225%, 0.224%, 0.223%, 0.222%, 0.221%, 0.220%, 0.219%, 0.218%, 0.217%, 0.216%, 0.215%, 0.214%, 0.213%, 0.212%, 0.211%, 0.210%, 0.209%, 0.208%, 0.207%, 0.206%, 0.205%, 0.204%, 0.203%, 0.202%, 0.201%, 0.200%, 0.199%, 0.198%, 0.197%, 0.196%, 0.195%, 0.194%, 0.193%, 0.192%, 0.191%, 0.190%, 0.189%, 0.188%, 0.187%, 0.186%, 0.185%, 0.184%, 0.183%, 0.182%, 0.181%, 0.180%, 0.179%, 0.178%, 0.177%, 0.176%, 0.175%, 0.174%, 0.173%, 0.172%, 0.171%, 0.170%, 0.169%, 0.168%, 0.167%, 0.166%, 0.165%, 0.164%, 0.163%, 0.162%, 0.161%, 0.160%, 0.159%, 0.158%, 0.157%, 0.156%, 0.155%, 0.154%, 0.153%, 0.152%, 0.151%, 0.150%, 0.149%, 0.148%, 0.147%, 0.146%, 0.145%, 0.144%, 0.143%, 0.142%, 0.141%, 0.140%, 0.139%, 0.138%, 0.137%, 0.136%, 0.135%, 0.134%, 0.133%, 0.132%, 0.131%, 0.130%, 0.129%, 0.128%, 0.127%, 0.126%, 0.125%, 0.124%, 0.123%, 0.122%, 0.121%, 0.120%, 0.119%, 0.118%, 0.117%, 0.116%, 0.115%, 0.114%, 0.113%, 0.112%, 0.111%, 0.110%, 0.109%, 0.108%, 0.107%, 0.106%, 0.105%, 0.104%, 0.103%, 0.102%, 0.101%, 0.100%, 0.099%, 0.098%, 0.097%, 0.096%, 0.095%, 0.094%, 0.093%, 0.092%, 0.091%, 0.090%, 0.089%, 0.088%, 0.087%, 0.086%, 0.085%, 0.084%, 0.083%, 0.082%, 0.081%, 0.080%, 0.079%, 0.078%, 0.077%, 0.076%, 0.075%, 0.074%, 0.073%, 0.072%, 0.071%, 0.070%, 0.069%, 0.068%, 0.067%, 0.066%, 0.065%, 0.064%, 0.063%, 0.062%, 0.061%, 0.060%, 0.059%, 0.058%, 0.057%, 0.056%, 0.055%, 0.054%, 0.053%, 0.052%, 0.051%, 0.050%, 0.049%, 0.048%, 0.047%, 0.046%, 0.045%, 0.044%, 0.043%, 0.042%, 0.041%, 0.040%, 0.039%, 0.038%, 0.037%, 0.036%, 0.035%, 0.034%, 0.033%, 0.032%, 0.031%, 0.030%, 0.029%, 0.028%, 0.027%, 0.026%, 0.025%, 0.024%, 0.023%, 0.022%, 0.021%, 0.020%, 0.019%, 0.018%, 0.017%, 0.016%, 0.015%, 0.014%, 0.013%, 0.012%, 0.011%, 0.010%, 0.009%, 0.008%, 0.007%, 0.006%, 0.005%, 0.004%, 0.003%, 0.002%, or 0.001% (wt/wt). In some embodiments, the retinoid agent is provided at a final concentration as recited in this paragraph, and is selected from retinol, retinal, retinyl acetate, retinaldehyde, retinyl palmitate, retinoic acid, retinyl propionate, retinyl linoleate, dehydroretinol, eretinate, eretrin, motretinide, tazarotene, isotretinoin, tretinoin, adapalene, bexarotene, fenretinide, and alitretinoin. In some embodiments, the retinoid agent is retinol, which provided at a final concentration as recited in this paragraph. In some embodiments, the retinoid agent is retinal, which provided at a final concentration as recited in this paragraph. In some embodiments, the retinoid agent is retinyl acetate, which provided at a final concentration as recited in this paragraph. In some embodiments, the retinoid agent is retinaldehyde, which provided at a final concentration as recited in this paragraph. In some embodiments, the retinoid agent is retinyl palmitate, which provided at a final concentration as recited in this paragraph. In some embodiments, the retinoid agent is retinoic acid, which provided at a final concentration as recited in this paragraph. In some embodiments, the retinoid agent is retinyl propionate, which provided at a final concentration as recited in this paragraph. In some embodiments, the retinoid agent is retinyl linoleate, which provided at a final concentration as recited in this paragraph. In some embodiments, the retinoid agent is dehydroretinol, which provided at a final concentration as recited in this paragraph. In some embodiments, the retinoid agent is eretinate, which provided at a final concentration as recited in this paragraph. In some embodiments, the retinoid agent is eretrin, which provided at a final concentration as recited in this paragraph. In some embodiments, the retinoid agent is motretinide, which provided at a final concentration as recited in this paragraph. In some embodiments, the retinoid agent is tazarotene, which provided at a final concentration as recited in this paragraph. In some embodiments, the retinoid agent is isotretinoin, which provided at a final concentration as recited in this paragraph. In some embodiments, the retinoid agent is tretinoin, which provided at a final concentration as recited in this paragraph. In some embodiments, the retinoid agent is adapalene, which provided at a final concentration as recited in this paragraph. In some embodiments, the retinoid agent is bexarotene, which provided at a final concentration as recited in this paragraph. In some embodiments, the retinoid agent is fenretinide, which provided at a final concentration as recited in this paragraph. In some embodiments, the retinoid agent is alitretinoin, which provided at a final concentration as recited in this paragraph.

As noted herein, it will be recognized by one of ordinary skill in the art upon study of the present document that in some cases it could be desirable to include further ingredients in the composition as described herein, e.g., salicylic acid, urea, alpha-hydroxy acids, beta-hydroxy acids.

For example, in some embodiments, the composition can additionally include salicylic acid. In some embodiments, the salicylic acid is provided in a final concentration of about 0.5, 1, 2, 3, 4, 5, 6, 7, 8, 9, 10, 15, 20, 30, 35, 40, 45, 50, 55, 60, 65, or 70% (wt/wt). Without wishing to be bound by theory or mechanism, the addition of salicylic acid can further increase the efficacy of some embodiments. The salicylic acid can result in epidermal desquamation of the hyperkeratosis, such that penetration of the composition is increased. It can also dilute or reduce the concentration of the retinoid agent, by altering the ratio of retinoid agent to imidazoquinoline compound (e.g., 5:1, 10:1, 20:1) so as to increase local tolerability and while maintaining efficacy.

For another example, in some embodiments, the composition can additionally include urea. In some embodiments, the urea is provided in a final concentration of about 0.5, 1, 2, 3, 4, 5, 6, 7, 8, 9, 10, 15, 20, 30, 35, 40, 45, 50, 55, 60, 65, or 70% (wt/wt). Without wishing to be bound by theory or mechanism, the addition of urea can further increase the efficacy of some embodiments. The urea can result in increased penetration. It can also dilute or reduce the concentration of the retinoid agent, by altering the ratio of retinoid agent to imidazoquinoline compound (e.g., 5:1, 10:1, 20:1) so as to increase local tolerability and while maintaining efficacy.

For another example, in some embodiments, the composition can additionally include alpha-hydroxy acid. In some embodiments, the alpha-hydroxy acid is provided in a final concentration of about 0.5, 1, 2, 3, 4, 5, 6, 7, 8, 9, 10, 15, 20, 30, 35, 40, 45, 50, 55, 60, 65, or 70% (wt/wt). Without wishing to be bound by theory or mechanism, the addition of alpha-hydroxy acid can further increase the efficacy of some embodiments. The alpha-hydroxy acid can result in epidermal desquamation of the hyperkeratosis, such that penetration of the composition is increased. It can also dilute or reduce the concentration of the retinoid agent, by altering the ratio of retinoid agent to imidazoquinoline compound (e.g., 5:1, 10:1, 20:1) so as to increase local tolerability and while maintaining efficacy.

For another example, in some embodiments, the composition can additionally include beta-hydroxy acid. In some embodiments, the beta-hydroxy acid is provided in a final concentration of about 0.5, 1, 2, 3, 4, 5, 6, 7, 8, 9, 10, 15, 20, 30, 35, 40, 45, 50, 55, 60, 65, or 70% (wt/wt). Without wishing to be bound by theory or mechanism, the addition of beta-hydroxy acid can further increase the efficacy of some embodiments. The beta-hydroxy acid can result in epidermal desquamation of the hyperkeratosis, such that penetration of the composition is increased. It can also dilute or reduce the concentration of the retinoid agent, by altering the ratio of retinoid agent to imidazoquinoline compound (e.g., 5:1, 10:1, 20:1) so as to increase local tolerability and while maintaining efficacy.

As will be apparent to one of ordinary skill in the art, further ingredients, such as vehicle enhancers can be provided in the composition of the presently-disclosed subject matter. Examples include, but are not limited to propylene glycol, cocamidopropyl betaine, oleamidoproplyl dimethylamine, propyl gallate, polyethylene glycol, and the like. Reference is also made to U.S. Patent Application Publication No. 2009/0182004, entitled "Imiquimod Formulation," which is incorporated herein by this reference.

In some embodiments, the composition is formulated for topical administration. In some embodiments, the composition can include a concentration of each active ingredient from about 1 to 30% in a carrier such as a pharmaceutical cream or gel base. Various formulations for topical use include, but are not limited to, drops, tinctures, lotions, creams, gels, solutions, ointments, lacquers. It is noted that the composition can also be associated with a device that contains the compositions and various supports and/or vehicles useful for delivery of the composition, for example, sticks (pins), tapes, occlusive applicators (e.g., cervical cap), and occlusive bandages. Such a device can be provided in a kit, together with the composition. The optimal percentage of the therapeutic agent in each pharmaceutical formulation varies according to the formulation itself and the therapeutic effect desired in the specific pathologies and correlated therapeutic.

As noted herein, the presently-disclosed subject matter further includes a method for the treatment of a condition affecting skin and/or a mucosal surface of a subject, which includes administering an effective amount of a composition, as described hereinabove, to the subject. In some embodiments, the composition is administered to an affected site on the skin or the mucosal surface of the subject. In some embodiments, the composition is administered topically, which can include direct administration to skin or mucosa, including intranasal, oral, and genital mucosa. In some embodiments, the composition can be injected, for example, administered by intralesional injection.

The presently-disclosed subject matter is further illustrated by the following specific but non-limiting examples. The following examples include some prophetic examples, as indicated. The following examples may include compilations of data that are representative of data gathered at various times during the course of development and experimentation related to the present invention.

EXAMPLES

Example 1—In Vivo Treatment of Warts

A composition including an imidazoquinoline compound; and a retinoid agent was tested in vivo. Imiquimod (5% (wt/wt)) and tazarotene (0.1% (wt/wt) were combined in a 1:1 ratio. The resulting composition was topically applied to individual warts in approximately 30 patients. The patients had various types of warts (thick and thin) in varying locations including palms, soles, hands, legs, feet, trunk, and extremities (including periungual). The composition could be used occluded or non-occluded, at the patient's option.

Figure 2:
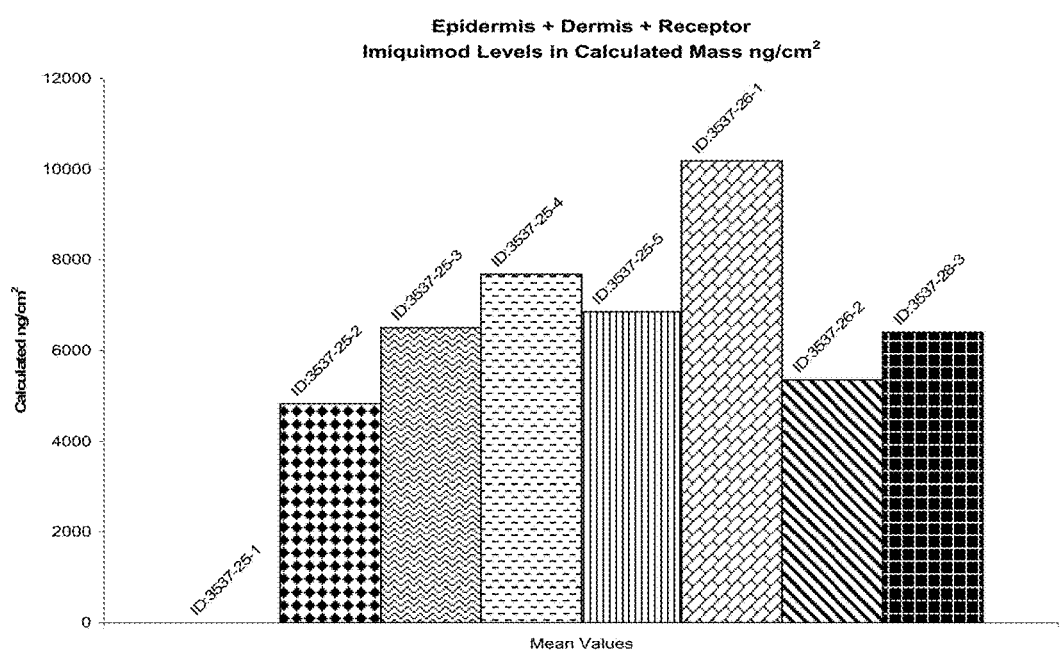
FIG. 2 is a bar graph showing cumulative penetration of Imiquimod following 24 hours of topical exposure in calculated $ng/cm^2$ penetrated based on a 5 $mg/cm^2$ dose.

With reference to FIGS. 1 and 2, the treatment resulted in marked improvement and resolution in many cases. This treatment was used with warts in multiple sites including the arms, legs, hands, feet, facial, and periungual areas with beneficial results. There was complete resolution in about 50% of the patients. There was about a 75%-90% reduction in size and number of warts in about 25% of the patients. There was about a 50%-75% reduction in size and number of warts in about 25% of the patients. The time for the patients to respond was about 1 week (in 5 of the patients) to about 3 months, with an average time to response of about 4-6 weeks. Some patients demonstrated a response including complete resolution without inflammation. The duration of response was shown to be prolonged in complete responders. Another noted benefit associated with the composition has been the resolution of warts at locally distant untreated sites (which may be due to increased immune recognition) as well as the decreased recurrence rate as compared to other modalities.

Patient follow-up showed no major tolerability issues. The composition was well-tolerated in the patients receiving treatment, with the most common side effect being a local minor irritation and sometimes a minor vesicular reaction (usually painless). The composition was reported to be easy to apply, convenient, and effective.

These results are in contrast to the results seen when applying imiquimod or tazarotene individually, which were not as efficacious. The composition resulted in surprisingly increased efficacy relative to the treatment with imiquimod or tazarotene individually.

Example 2—In Vivo Treatment of Skin Conditions (Prophetic)

A composition including an imidazoquinoline compound; and a retinoid agent is tested in vivo. The composition is topically applied to sites displaying a skin condition selected from a wart, molluscum contagiosum, a keloid, and a skin cancer, each as defined herein. The treatment results in marked improvement and resolution in many cases. The results are found to be more efficacious as compared to applying an imidazoquinoline compound or a retinoid agent individually.

Example 3—In Vivo Treatment of Skin Conditions Effecting Mucosal Surface (Prophetic)

A composition including an imidazoquinoline compound; and a retinoid agent is tested in vivo. The composition includes a concentration of retinoid agent (e.g., tazarotene) that is sufficiently low so as not to cause undue irritation to the mucosal surface (e.g., mouth or genitalia) of a patient. The composition is topically applied to sites displaying a skin condition selected from a wart, molluscum contagiosum, a keloid, and a skin cancer, each as defined herein. The treatment results in marked improvement and resolution in many cases. The results are found to be more efficacious as compared to applying an imidazoquinoline compound or a retinoid agent individually. Surprisingly, the inclusion of the retinoid agent, even at a concentration sufficiently low so as not to cause undue irritation to the mucosal surface, results in unexpected beneficial results.

Example 5—Synergy Coefficient (Prophetic)

An animal model of hyperkeratinized skin is used to test the efficacy of an exemplary composition and the efficacy of imiquimod for treating common warts. The exemplary composition includes 5% (wt/wt) imiquimod and a 0.1% (wt/wt) tazarotene.

The comparison compound is imiquimod. Administration of the composition results in a 100% cure rate, while the treatment with imiquimod results in a 60% cure rate.

The activity ratio is calculated as follows:

$$R=AB/X_n=100/60=1.67.$$

The concentration adjustment factor is calculated as follows:

$$F=100/C_n=100/5=20.$$

The synergy coefficient is therefore:

$$S=(R)(F)=(1.67)(20)=33.34; \text{ or}$$

$$S=[(AB/X_n)(100)]/C_n=[(100/60)(100)]/5=33.34$$

The experiment is repeated, wherein the comparison compound is tazarotene. Administration of the composition results in a 100% cure rate, while the treatment with tazarotene results in a 40% cure rate.

According to Formula 1, the activity ratio is calculated as follows:

$$R=AB/X_n=100/40=2.5$$

According to Formula 2, the concentration adjustment factor is calculated as follows:

$$F=100/C_n=100/0.1=1000$$

According to Formulae 3 and 4, the synergy coefficient is therefore:

$$S=(R)(F)=(2.5)(1000)=2500; \text{ or}$$

$$S=[(AB/X_n)(100)]/C_n=[(100/40)(100)]/0.1=2500$$

Based on the measured % effect of imiquimod (60%) and tazarotene (40%), the expected % effect of the combination is calculated according to Formula 5, as follows:

$$E=X+Y-(X*Y/100)=60+40-(60*40/100)=76$$

The actual % effect of the composition is 100% (A=100). Because A=100>E=76, the combination has synergy (a positive interaction of the compounds).

Example 6—Solubility, Compatibility, and Stability of the Composition

The composition feasibility of a composition including both imiquimod and tazarotene was studied. Goals of the study included the following: to determine whether the imidazoquinoline compound and the retinoid agent are compatible with each other, to determine whether common solvents could be used to sufficiently dissolve the two ingredients, and to determine whether the resulting composition would be stable. The ability to produce a stable and compatible composition was uncertain at the outset of these studies, in part, given that imiquimod is well known to be a challenging molecule.

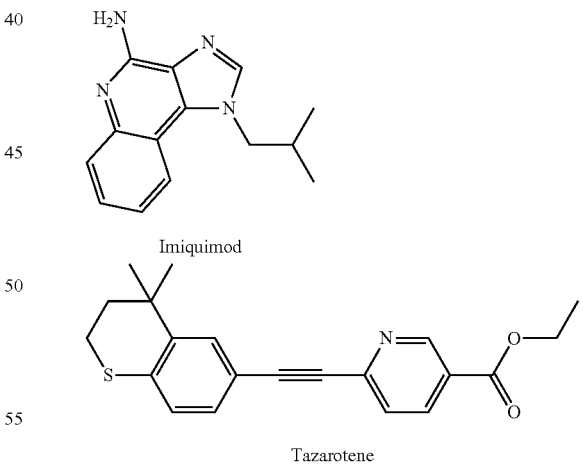

Imiquimod

Tazarotene

For this example, isostearic acid (ISA) was selected as a primary solvent, and the following additional solvents were selected based on miscibility with ISA and solubility of tazarotene: alcohol (A) (ethyl alcohol, USP (190 Proof)), benzyl alcohol (BA), diethyl sebacate (DES), mineral oil (MO), and transcutol (T).

The compositions having solvent blends as outlined in Table 1 were prepared to evaluate the compatibility of imiquimod (5% wt/wt) and tazarotene (0.1% wt/wt).

TABLE 1

Solvent Blends for to Test Compatibility of Imiquimod and Tazarotene

50:50 Isostearic Acid and Alcohol (ISA + A)
50:50 Isostearic Acid and Benzyl Alcohol (ISA + BA)
50:50 Isostearic Acid and Diethyl Sebacate (ISA + DES)
50:50 Isostearic Acid and Mineral Oil (ISA + MO)
50:50 Isostearic Acid and Transcutol (ISA + T)

Control Samples for each solution (T=0) were provided using the initial samples stored at 5° C., and analyzed after four (4) weeks. Test Samples of each solution were subjected to the following conditions: 1) storage at 25° C. for four weeks; 2) storage at 40° C. for four weeks; 3) storage at 50° C. for four weeks; and 4) three cycles of freeze/warm (F/W) cycling (−20° C. to 40° C.). The physical stability of each Sample was observed and the chemical stability of imiquimod and tazarotene in each Sample was studied using chromatographic techniques.

Information regarding Physical Stability is set forth in Table 2.

TABLE 2

Physical Stability

| Batch 3537-18 | Description | T = 0 | 3 cycles F/W | 4 weeks 25° C. | 4 weeks 40° C. | 4 weeks 50° C. |
|---|---|---|---|---|---|---|
| 2 | ISA + A | pale yellow clear solution | Conforms | Conforms | Conforms | Conforms |
| 3 | ISA + BA | pale yellow clear solution | Conforms | Conforms | Conforms | Conforms |
| 4 | ISA + DES | pale yellow clear solution | Conforms | Conforms | Conforms | Conforms |
| 5 | ISA + MO | colorless to pale yellow, clear solution | Conforms | Conforms | Conforms | Conforms |
| 6 | ISA + T | colorless to pale yellow, clear solution | Conforms | Conforms | *pale yellow solution, crystals settled at bottom | *pale yellow solution, crystals settled at bottom |

Note:
"Conforms" indicates appearance meets T = 0 evaluation

Information regarding Chemical Stability is set forth in Tables 3-8.

TABLE 3

Summary of Imiquimod Stability

Imiquimod % Label Claim (degs, % Area)

| Description | T = 0 | 3 cycles F/W | 4 weeks 25° C. | 4 weeks 40° C. | 4 weeks 50° C. |
|---|---|---|---|---|---|
| ISA + A | 102.3 | 101.9 | 102.9 | 102.1 | 102.6 (0.08) |
| ISA + BA | 101.3 | 101.3 (0.22) | 101.5 | 102.2 (0.26) | 101.5 (0.36) |
| ISA + DES | 100.6 | 101.5 | 101.1 | 102.1 | 101.3 |
| ISA + MO | 101.4 | 102.4 | 101.4 | 101.7 | 101.8 |
| ISA + T | 102.0 | 101.9 | 101.5 | Not analyzed | Not analyzed |

Note:
Mean values are reported

TABLE 4

Summary of Tazarotene Stability

Tazarotene % Label Claim (degs, % Area)

| Batch 3537-18 | Description | T = 0 | 3 cycles F/W | 4 weeks 25° C. | 4 weeks 40° C. | 4 weeks 50° C. |
|---|---|---|---|---|---|---|
| 2 | ISA + A | 101.5 | 100.3 (0.19) | 102.6 | 100.8 (0.18) | 99.9 (0.34) |
| 3 | ISA + BA | 78.6 (0.42) | 66.0 (1.35) | 76.2 (0.51) | 63.8 (1.59) | 57.8 (1.76) |
| 4 | ISA + DES | 100.0 | 99.4 | 100.8 | 99.5 | 99.1 |
| 5 | ISA + MO | 100.9 | 99.9 | 100.5 | 98.4 | 99.1 |
| 6 | ISA + T | 101.6 | 91.4 (0.49) | 100.7 | Not analyzed | Not analyzed |

Note:
Mean values are reported

TABLE 5

Tazarotene and Imiquimod Solution Stability Summary Report

| | | Imiquimod | | | Tazarotene | | |
| --- | --- | --- | --- | --- | --- | --- | --- |
| Description | Condition | % LC | Degradation Products (RRT) | % Area | % LC | Degradation Products (RRT) | % Area |
| 50:50 Isostearic Acid and Alcohol | T = 0 | 100.9 | NC | NA | 100.2 | ND | NA |
| | | 103.6 | ND | NA | 102.8 | ND | NA |
| | Freeze/Warm (−20° C./40° C. | 100.8 | ND | NA | 99.3 | 0.92 | 0.19 |
| | | 103.0 | ND | NA | 101.3 | 0.92 | 0.19 |
| | 4 weeks at 25° C. | 102.7 | ND | NA | 102.6 | ND | NA |
| | | 103.0 | ND | NA | 102.5 | ND | NA |
| | 4 weeks at 40° C. | 101.4 | ND | NA | 100.3 | 0.92 | 0.16 |
| | | 102.7 | ND | NA | 101.2 | 0.92 | 0.19 |
| | 4 weeks at 50° C. | 102.9 | 1.22 | 0.08 | 99.8 | 0.92 | 0.32 |
| | | 102.2 | 1.22 | 0.08 | 100.0 | 0.92 | 0.35 |

TABLE 6

Tazarotene and Imiquimod Solution Stability Summary Report

| | | Imiquimod | | | Tazarotene | | |
| --- | --- | --- | --- | --- | --- | --- | --- |
| Description | Condition | % LC | Degradation Products (RRT) | % Area | % LC | Degradation Products (RRT) | % Area |
| 50:50 Isostearic Acid and Benzyl Alcohol | T = 0 | 100.5 | ND | NA | 78.3 | 0.84 | 0.41 |
| | | 102.0 | ND | NA | 78.9 | 0.84 | 0.42 |
| | Freeze/Warm (−20° C./40° C. | 100.9 | 1.71 | 0.23 | 65.8 | 0.84 | 0.75 |
| | | | | | | 1.05 | 0.53 |
| | | | | | | | Total: 1.27 |
| | | 101.7 | 1.71 | 0.21 | 66.2 | 0.84 | 0.94 |
| | | | | | | 1.05 | 0.48 |
| | | | | | | | Total: 1.42 |
| | 4 weeks at 25° C. | 101.7 | ND | NA | 76.3 | 0.84 | 0.46 |
| | | 101.3 | N/D | NA | 76.0 | 0.84 | 0.55 |
| | 4 weeks at 40° C. | 102.4 | 1.71 | 0.26 | 63.7 | 0.84 | 1.03 |
| | | | | | | 1.05 | 0.59 |
| | | | | | | | Total: 1.62 |
| | | 101.9 | 1.71 | 0.25 | 63.8 | 0.85 | 0.97 |
| | | | | | | 1.05 | 0.59 |
| | | | | | | | Total: 1.56 |
| | 4 weeks at 50° C. | 101.4 | 1.71 | 0.31 | 57.7 | 0.84 | 1.18 |
| | | | | | | 1.05 | 0.79 |
| | | | | | | | Total: 1.97 |
| | | 101.6 | 1.71 | 0.40 | 57.9 | 0.84 | 1.01 |
| | | | | | | 1.05 | 0.54 |
| | | | | | | | Total: 1.55 |

TABLE 7

Tazarotene and Imiquimod Solution Stability Summary Report

| | | Imiquimod | | | Tazarotene | | |
| --- | --- | --- | --- | --- | --- | --- | --- |
| Description | Condition | % LC | Degradation Products (RRT) | % Area | % LC | Degradation Products (RRT) | % Area |
| 50:50 Isostearic Acid and | T = 0 | 101.3 | ND | NA | 100.5 | ND | NA |
| | | 99.9 | ND | NA | 99.5 | ND | NA |
| | Freeze/Warm | 101.6 | ND | NA | 99.4 | ND | NA |

TABLE 7-continued

Tazarotene and Imiquimod Solution Stability Summary Report

| | | Imiquimod | | | Tazarotene | | |
| --- | --- | --- | --- | --- | --- | --- | --- |
| Description | Condition | % LC | Degradation Products (RRT) | % Area | % LC | Degradation Products (RRT) | % Area |
| Diethyl Sebacate | (−20° C./40° C.) | 101.3 | ND | NA | 99.3 | ND | NA |
| | 4 weeks at 25° C. | 100.9 | ND | NA | 100.8 | ND | NA |
| | | 101.3 | ND | NA | 100.8 | ND | NA |
| | 4 weeks at 40° C. | 102.3 | ND | NA | 99.7 | ND | NA |
| | | 101.8 | ND | NA | 99.2 | ND | NA |
| | 4 weeks at 50° C. | 101.7 | ND | NA | 99.3 | ND | NA |
| | | 100.9 | ND | NA | 98.8 | ND | NA |

TABLE 8

Tazarotene and Imiquimod Solution Stability Summary Report

| | | Imiquimod | | | Tazarotene | | |
| --- | --- | --- | --- | --- | --- | --- | --- |
| Description | Condition | % LC | Degradation Products (RRT) | % Area | % LC | Degradation Products (RRT) | % Area |
| 50:50 Isostearic Acid and Mineral Oil | T = 0 | 100.5 | ND | NA | 100.3 | ND | NA |
| | | 102.3 | ND | NA | 101.4 | ND | NA |
| | Freeze/Warm (−20° C./40°C.) | 102.9 | ND | NA | 100.1 | ND | NA |
| | | 101.8 | ND | NA | 99.7 | ND | NA |
| | 4 weeks at 25° C. | 101.7 | ND | NA | 100.4 | ND | NA |
| | | 101.0 | ND | NA | 100.5 | ND | NA |
| | 4 weeks at 40° C. | 102.1 | ND | NA | 98.8 | ND | NA |
| | | 101.2 | ND | NA | 97.9 | ND | NA |
| | 4 weeks at 50° C. | 101.9 | ND | NA | 99.3 | ND | NA |
| | | 101.6 | ND | NA | 98.8 | ND | NA |

As reflected by the results presented above, the physical stability of imiquimod and tazarotene combination is shown for all Samples, with the exception of the samples including isostearic acid and transcutol (ISA+T) stored at high temperatures (40-50° C.).

As also reflected by the results presented above, in all Samples analyzed, imiquimod was shown to be chemically stable, based on the fact that the mean assay values remained relatively unchanged from the initial values over 4 weeks at various temperatures.

As further reflected by the results presented above, Tazarotene is chemically stable in all the solvent blends with the exception of isostearic acid and benzyl alcohol (ISA+BA), in which it appears that BA has a negative impact on the chemical stability of tazarotene and appears to result in a temperature dependant loss of tazarotene. Tazarotene stability also appears to be impacted by exposure to F/W cycling in ISA+T.

To summarize, all analyzed Samples displayed both physical and chemical stability under certain conditions, including storage at room temperature (25° C.). Furthermore, compositions of imiquimod and tazarotene in ISA plus alcohol, diethyl sebacate, or mineral oil were both physically and chemically stable under all test conditions, including storage for four weeks at 5° C., 25° C., 40° C., and 50° C., as well as conditions including three rounds of freeze/warm cycling.

Example 7—In Vitro Percutaneous Absorption Studies Using Human Tissue

To characterize the effect of providing a composition including both an imidazoquinoline compound and a retinoid agent on the penetration of the composition as compared to an imidazoquinoline compound alone, absorption studies were conducted using human tissue. For the study described in this example, varying concentrations of tazarotene were evaluated while keeping the concentration of imiquimod constant (5% w/w).

Data from this in vitro skin permeation study indicate a trend in the efficiency of delivery of Imiquimod. Imiquimod delivery, expressed as a sum of all the delivery values for each of the three evaluated compartments, has a consistent response to the addition of Tazarotene: Delivery of Imiquimod increases with the addition of Tazarotene.

DMSO based controls are used because they usually yield higher delivery of actives through the skin. In this case, the DMSO control (which included Tazarotene) did not give a higher degree of penetration, indicating that imiquimod delivery is independent of the choice of solvent, but instead is due to the addition of tazarotene.

Methods

This in vitro percutaneous absorption study was conducted using procedures adapted from the FDA and AAPS Report of the Workshop on Principles and Practices of In Vitro Percutaneous Penetration Studies: Relevance to Bioavailability and Bioequivalence (Skelly et al., 1987). All evaluated compositions were prepared by DPSI. The compositions of all the compositions evaluated in this study are summarized in Table 9.

TABLE 9

Test Samples

| Sample ID* | Description | % (w/w) Tazarotene | % (w/w) Imiquimod |
|---|---|---|---|
| 3537-25-1 | Tazarotene (T) | 0.10 | 0.00 |
| 3537-25-2 | Imiquimod (I) | 0.00 | 5.00 |
| 3537-25-3 | 1:500 | 0.01 | 5.00 |
| 3537-25-4 | 1:100 | 0.05 | 5.00 |
| 3537-25-5 | 1:50 | 0.10 | 5.00 |
| 3537-26-1 | 1:10 | 0.50 | 5.00 |
| 3537-26-2 | 1:5 | 1.00 | 5.00 |
| 3537-26-3 | DMSO | 0.10 | 5.00 |
| 3537-28-3** | Control-1:50 | | |

*All samples were provided in 50:50 Isostearic Acid and Alcohol (ISA + A), except the DMSO Control, which was provided in 80:20 DMSO and Isostearic Acid.
**Sample IDs 3537-28-3 is identical to 3537-26-3.
Sample IDs 3537-28-3 and 3537-25-1 were used as positive and negative controls for Imiquimod permeation, respectively.

The clinically relevant dose of 5 mg/cm$^2$ was applied to dermatomed human abdominal tissue from a single donor obtained following elective surgery. The thickness of the tissue ranged from 0.023-0.032 inches (0.584-0.813 mm) with a mean+/−standard deviation in thickness of 0.027+/−0.003 inches (0.677+/−0.066 mm) and a coefficient of variation of 10%.

Percutaneous absorption was evaluated using this human abdominal tissue from a single donor mounted in Bronaugh flow-through diffusion cells. The cells were maintained at a constant temperature of 32° C. by use of recirculating water baths. These cells have a nominal diffusion area of 0.64 cm$^2$. Fresh receptor phase (PBS, pH 7.4, containing 0.1% sodium azide and 4% Bovine Serum Albumin) was continuously pumped under the tissue at a flow rate of nominally 0.25 ml/hr and collected in 6-hour intervals. The receptor phase samples were collected in pre-weighed scintillation vials; the post weights were taken at the end of the study. Following the 24-hour duration exposure, the composition residing on the tissue surface was removed by tape-stripping with CuDerm D-Squame stripping discs. The epidermis, dermis, and receptor phase samples were labeled and frozen prior to subsequent analysis of Tazarotene and Imiquimod content by LC/MS/MS and ultimate sample disposal.

Tissue permeation and deposition results were statistically evaluated using unpaired student's t-tests (significant differences between compositions were defined by a p-value of <0.05, at the 95% confidence interval).

Results

Epidermis, Dermis, and Receptor.

With reference to Table 10, Column 5, data showing cumulative penetration of imiquimod based on a 5 mg/cm$^2$ dose is presented as percent of applied dose (Sub-column A) and calculated ng/cm$^2$ following a theroretical dose of 5 mg composition/cm$^2$.

With regard to efficiency of delivery, the total amount of imiquimod present ranged from 1.93 to 4.07 percent of the applied dose of Imiquimod. Compositions 3537-25-4 and 3537-26-1 had the highest efficiency of delivery with 3.07 and 4.07 perecent of the applied dose of Imiquimod, respectively. Composition 3537-25-2, the only composition that did not contain tazarotene, exhibited the least efficient delivery with 1.93 percent of the applied dose.

With regard to total amount of Imiquimod delivered, the calculated amount ranged from 4833 to 10186 ng/cm$^2$. Compositions 3537-25-4 and 3537-26-1 had the highest total Imiquimod with 7682 and 10186 ng/cm$^2$, respectively. Composition3537-25-2, the only composition that did not contain tazarotene, generated the lowest total levels of Imiquimod, with 4833 ng/cm$^2$. The data presented in Table 10, Column 5, Sub-column B are presented graphically in FIG. 2.

TABLE 10

Cumulative Receptor Phase and Tissue Levels of Imiquimod Following 24 Hours of Topical Exposure

| Formulation ID | | Receptor Content at 24 Hours | | Epidermis | | Dermis | | Dermis + Receptor Mean | | Epidermis + Dermis + Receptor Mean | |
|---|---|---|---|---|---|---|---|---|---|---|---|
| | | % Dose Applied | Calculated ng/cm$^2$ Api for Formulation Dose of 5 mg/cm2 | % Dose Applied | Calculated ng/cm2 Api for Formulation Dose of 5 mg/cm2 | % Dose Applied | Calculated ng/cm2 Api for Formulation Dose of 5 mg/cm2 | % Dose Applied | Calculated ng/cm2 Api for Formulation Dose of 5 mg/cm2 | % Dose Applied | Calculated ng/cm2 Api for Formulation Dose of 5 mg/cm2 |
| A) ID: 3537-25-1 | Mean | 0.00 | 0.00 | 0.00 | 0.00 | 0.00 | 0.00 | 0.00 | 0.00 | 0.00 | 0.00 |
| | SD | 0.00 | 0.00 | 0.00 | 0.00 | 0.00 | 0.00 | | | | |
| | % CV | N/A | N/A | N/A | N/A | N/A | N/A | | | | |
| B) ID: 3537-25-2 | Mean | 0.018 | 46.2 | 1.80 | 4492 | 0.118 | 295 | 0.136 | 341 | 1.93 | 4833 |
| | SD | 0.008 | 20.5 | 0.52 | 1292 | 0.028 | 71 | | | | |
| | % CV | 44 | 44 | 29 | 29 | 24 | 24 | | | | |
| C) ID: 3537-25-3 | Mean | 0.018 | 44.2 | 2.40 | 5991 | 0.186 | 466 | 0.204 | 510 | 2.60 | 6501 |
| | SD | 0.006 | 16.0 | 0.39 | 985 | 0.097 | 243 | | | | |
| | % CV | 36 | 36 | 16 | 16 | 52 | 52 | | | | |
| D) ID: 3537-25-4 | Mean | 0.016 | 39.1 | 2.79 | 6971 | 0.269 | 672 | 0.284 | 711 | 3.07 | 7682 |
| | SD | 0.005 | 13.3 | 1.00 | 2489 | 0.217 | 543 | | | | |
| | % CV | 34 | 34 | 36 | 36 | 81 | 81 | | | | |
| E) ID: 3537-25-5 | Mean | 0.015 | 37.2 | 2.53 | 6331 | 0.193 | 483 | 0.208 | 520 | 2.74 | 6851 |
| | SD | 0.005 | 12.5 | 0.79 | 1982 | 0.102 | 255 | | | | |
| | % CV | 34 | 34 | 31 | 31 | 53 | 53 | | | | |
| F) ID: 3537-26-1 | Mean | 0.016 | 40.3 | 3.76 | 9405 | 0.296 | 741 | 0.312 | 781 | 4.07 | 10186 |
| | SD | 0.005 | 11.9 | 1.33 | 336 | 0.164 | 410 | | | | |
| | % CV | 29 | 29 | 35 | 35 | 55 | 55 | | | | |
| G) ID: 3537-26-2 | Mean | 0.024 | 60.1 | 1.93 | 4830 | 0.186 | 466 | 0.211 | 526 | 2.14 | 5356 |
| | SD | 0.028 | 70.8 | 0.55 | 1380 | 0.080 | 200 | | | | |
| | % CV | 118 | 118 | 29 | 29 | 43 | 43 | | | | |

TABLE 10-continued

Cumulative Receptor Phase and Tissue Levels of Imiquimod Following 24 Hours of Topical Exposure

| Formulation ID | | Receptor Content at 24 Hours | | Epidermis | | Dermis | | Dermis + Receptor Mean | | Epidermis + Dermis + Receptor Mean | |
|---|---|---|---|---|---|---|---|---|---|---|---|
| | | % Dose Applied | Calculated ng/cm² Api for Formulation Dose of 5 mg/cm² | % Dose Applied | Calculated ng/cm2 Api for Formulation Dose of 5 mg/cm2 | % Dose Applied | Calculated ng/cm2 Api for Formulation Dose of 5 mg/cm2 | % Dose Applied | Calculated ng/cm2 Api for Formulation Dose of 5 mg/cm2 | % Dose Applied | Calculated ng/cm2 Api for Formulation Dose of 5 mg/cm2 |
| H) ID: 3537-28-3 | Mean | 0.026 | 63.9 | 2.27 | 5667 | 0.268 | 670 | 0.294 | 734 | 2.56 | 6401 |
| | SD | 0.005 | 11.5 | 0.58 | 1449 | 0.105 | 263 | | | | |
| | % CV | 18 | 18 | 26 | 26 | 39 | 39 | | | | |

Efficiency of Delivery

Tissue permeation and deposition of Imiquimod are summarized in Table 10 and presented in units of percent of applied dose and calculated ng/cm² following a theoretical dose of 5 mg composition/cm².

Tissue permeation (receptor phase levels). With reference to Table 10, Column 1, Sub-Column A, tissue permeation (receptor phase levels) after 24 hours ranged from 0.015 to 0.026 percent of the applied dose of Imiquimod.

Dermal deposition. With reference to Table 10, Column 3, Sub-Column A, dermal deposition of Imiquimod from the evaluated compositions ranged from 0.118 to 0.296 percent of the applied dose. Composition 3537-25-4 and 3537-26-1 had the highest efficiency of Imiquimod dermal deposition with 0.269 and 0.296 percent of the applied dose respectively. The lowest efficiency of Imiquimod dermal deposition was produced by Composition 3537-25-2 with 0.118% percent of the applied dose.

Epidermal deposition. With reference to Table 10, Column 2, Sub-Column A, epidermal deposition of Imiquimod from the evaluated compositions ranged from 1.80 to 3.76 percent of the applied dose. Compositions 3537-25-4 and 3537-26-1 had the highest efficiency of Imiquimod epidermal deposition with 2.79 and 3.76 percent of the applied dose, respectively. The lowest efficiency of Imiquimod epidermal deposition was generated by Composition 3537-25-2.

Total Amount Delivered

Figure 3:
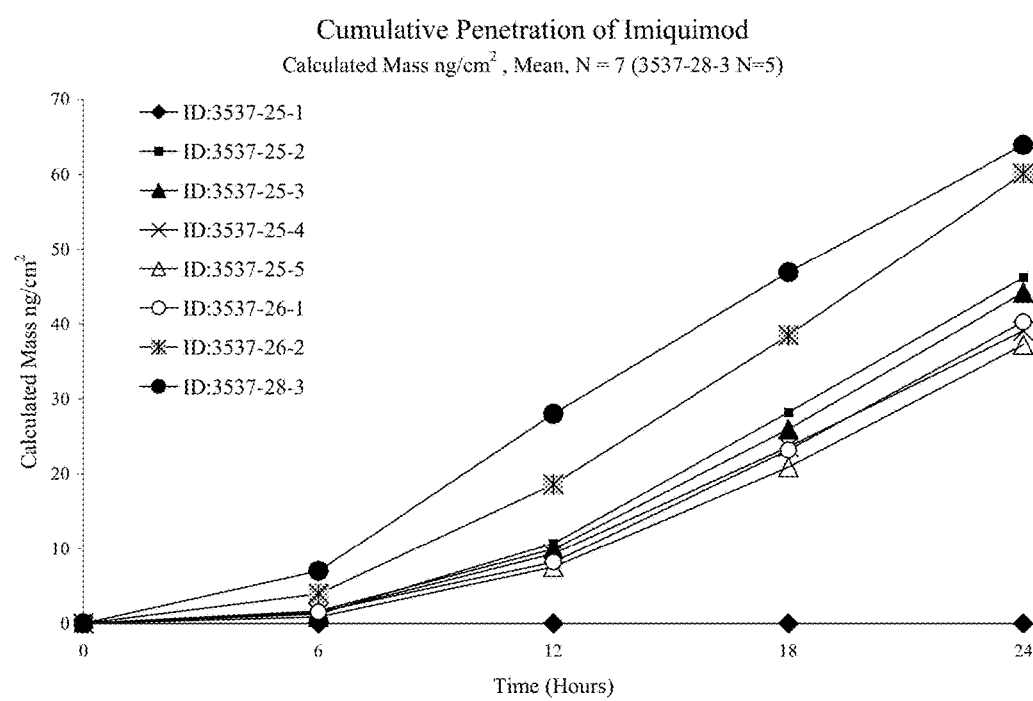
FIG. 3 is a time course showing cumulative receptor phase levels of Imiquimod in calculated $ng/cm^2$ penetrated based on a 5 $mg/cm^2$ dose.

Tissue permeation (receptor phase levels). With reference to Table 10, Column 1, Sub-Column B, the total amount of Imiquimod delivered from a composition is dependent upon the concentration of Imiquimod in the product as well as the efficiency of delivery (percent of applied dose). Calculated mass of Imiquimod permeating the tissue following a dose of 5 mg composition per square centimeter of skin for 24 hours (receptor phase levels) ranged from 37.2 to 60.1 ng/cm² of Imiquimod. Compositions 3537-25-2 and 3537-26-2 had the highest delivery of Imiquimod with 46.2 and 60.1 ng/cm², respectively, whereas the lowest efficiency of Imiquimod delivery was with 3537-25-5. A kinetic profile of tissue permeation is presented in FIG. 3, where the cumulative tissue permeation of Imiquimod in units of ng/cm² is plotted against time in hours.

Figure 4:
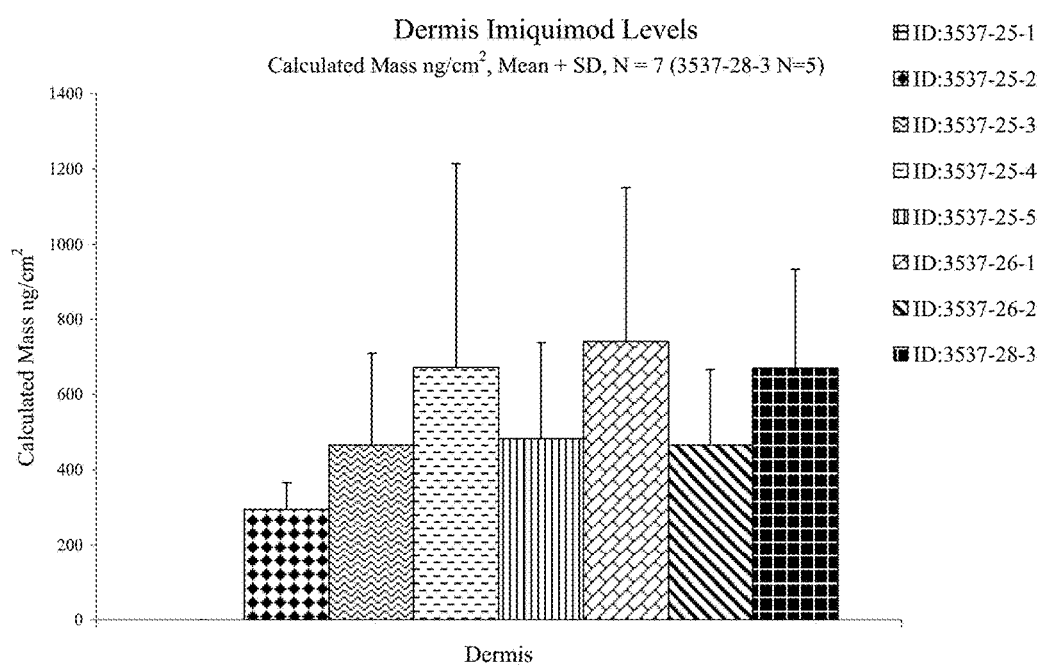
FIG. 4 is a bar graph showing dermal levels of Imiquimod following 24 hours of topical exposure in calculated $ng/cm^2$ Imiquimod based on a 5 $mg/cm^2$ dose.

Dermal deposition. With reference to Table 10, Column 3, Sub-Column B, the calculated Imiquimod dermal deposition ranged from 295 to 741 ng/cm². Compositions 3537-25-4 and 3537-26-1 had the highest Imiquimod dermal deposition with 672 and 741 ng/cm², respectively. Composition 3537-25-2 Composition produced the lowest Imiquimod dermal deposition, 295 ng/cm². These results are presented graphically in FIG. 4, which shows dermal levels of Imiquimod following 24 hour duration of topical exposure in unit(s) of ng/cm².

Figure 5:
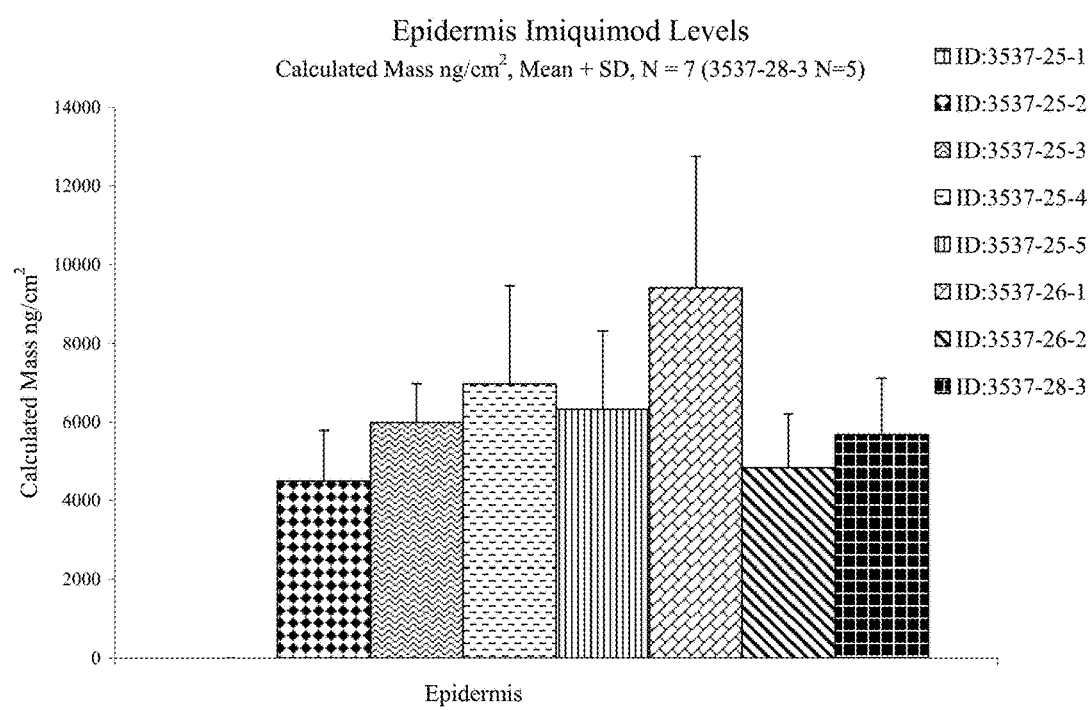
FIG. 5 is a bar graph showing epidermal levels of Imiquimod following 24 hours of topical exposure in calculated $ng/cm^2$ Imiquimod based on a 5 $mg/cm^2$ dose.

Epidermal deposition. With reference to Table 10, Column 2, Sub-Column B, the calculated Imiquimod epidermal deposition ranged from 4,492 to 9,405 ng/cm². Compositions 3537-25-4 and 3537-26-1 had the highest Imiquimod epidermal deposition with 6,971 and 9,405 ng/cm², respectively. Composition 3537-25-2 generated the lowest Imiquimod epidermal deposition, 4,492 ng/cm². These results are presented graphically in FIG. 5, which shows epidermal levels of Imiquimod following 24 hour duration of topical exposure in unit(s) of ng/cm².

Figure 6:
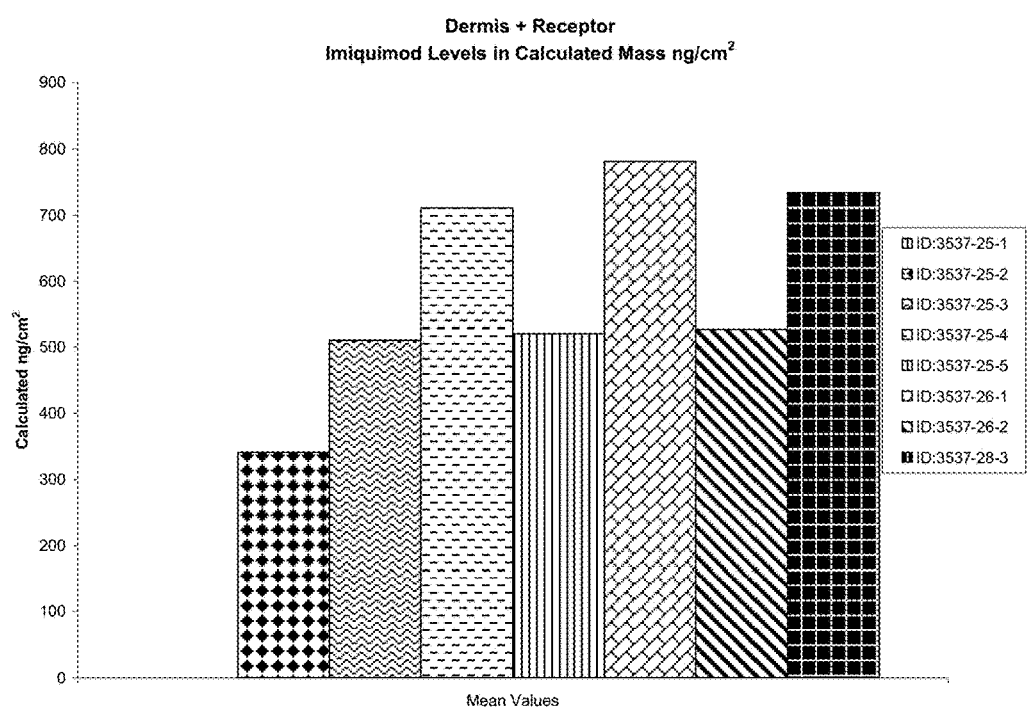
FIG. 6 is a bar graph showing dermis plus receptor levels of Imiquimod following 24 hours of topical exposure in calculated $ng/cm^2$ Imiquimod based on a 5 $mg/cm^2$ dose.

Dermis and Receptor (combined values). With reference to Table 10, Column 4, Sub-Column B, the total amount of Imiquimod present in the dermal and receptor compartments was assessed by calculating the total calculated mass/cm² [ng/cm²] for a composition dose of 5 mg/cm² present in the dermis (D) and receptor (R) compartments. Subsequently, the mean values of six replicates were determined and defined as D+R. The calculated mean D+R values provided an indication of the total amount of API that penetrated the epidermis. Mean D+R ranged from 341 to 781 ng/cm² of Imiquimod. Compositions 3537-25-4 and 3537-26-1 yielded the highest D+R values, respectively. The lowest D+R was associated with Composition 3537-25-2. These results are presented graphically in FIG. 6, which shows D+R levels of Imiquimod following 24 hour duration of topical exposure in unit(s) of ng/cm².

CONCLUSIONS

Data from this study demonstrate a trend in the efficiency of delivery of Imiquimod. Imiquimod delivery, expressed as a sum of all the delivery values for each of the three evaluated compartments, has a consistent response to the addition of Tazarotene: Delivery of Imiquimod increases with the addition of Tazarotene.

With reference to FIG. 2, showing the cumulative penetration of Imiquimod, the data consistently show that any addition of tazarotene to the composition will improve the penetration of imiquimod, surprisingly, even at concentrations as much as 10 times lower (0.01% (w/w)) than the concentration at which tazarotene is currently in clinical use (0.1% (w/w)). Unexpectedly, compositions including doses of tazarotene as low as 0.01% appear to provide for similar levels of penetration as compared to compositions including a 0.1% concentration of tazarotene. Also, surprisingly, it appears that concentrations of tazarotene that are higher (1%) or relatively higher as compared to imiquimod (1:5 ratio) were less effective than lower concentrations.

Another unexpected finding was associated with the positive control (3537-28-3), which contained DMSO, but apart from the solvent was identical to composition 3537-25-5. DMSO based controls are used because they usually yield higher delivery of actives through the skin. In this case, the DMSO control (which included Tazarotene) did not give a higher degree of penetration, indicating that imiquimod delivery is independent of the choice of solvent, but instead is due to the addition of tazarotene. Indeed, as compared to the sample including Imiquimod without tazarotene (3537-25-2), all test samples including any concentration of tazarotene were found to improve penetration of Imiquimod.

As contemplated by the present inventor, composition including imiquimod and tazarotene have increased penetration, as compared to imiquimod individually. It is believed that the increased penetration can be correlated to an increased effectiveness of imiquimod. Without wishing to be bound by theory or mechanism, the increased penetration is believed to result from an ability of tazarotene to decrease the thickness of a layer of keratin in the virally infected cells. Tazarotene also decreases keratinocyte proliferation and increases the maturation phase of the virally infected cells thus thinning the thick skin that often covers warts. The combination also allows for a dilution of the tazarotene and its potential for local irritancy. Indeed, with the surprising efficacy at lower concentrations of tazarotene, certain embodiments of the composition can be readily prepared to limit irritancy and/or for areas prone to irritation. The compositions of the presently-disclosed subject matter will allow for increased tolerance, efficacy, compliance, and ease of use. When the imiquimod and tazarotene are used separately, the effects of both are diminished, and if applied at different points in time there is a decrease in compliance as well as the loss of the beneficial effect noted when utilized simultaneously in compositions of the presently-disclosed subject matter.

As noted herein, synergistic clinical results are achieved by combining an imidazoquinoline compound and a retinoid agent in a single composition. Without wishing to be bound by theory or mechanism, in addition to benefits achieved due to increased penetration of the imidazoquinoline compound, as facilitated by the retinoid agent, each component of the composition has an active role in treating the condition of interest, and each improves the effect of the other by virtue of being provided in a single composition for administration. For example, in addition to increasing the penetration of the imidazoquinoline compound, the retinoid agent has an effect in treating the condition of interest, and such effect is improved in the presence of the imidazoquinoline compound. Similarly, in addition to having increased penetration in the presence of the retinoid agent, the imidazoquinoline compound has an improved effect in treating the condition of interest in the presence of the retinoid agent. In this regard, the combination of the imidazoquinoline compound and the retinoid agent can achieve synergistic results in the treatment of a condition affecting skin and/or a mucosal surface of a subject, which are in addition to mere additive effect. In some embodiments, the synergistic results are in addition to effects resulting from increased penetration of the imidazoquinoline compound in the presence of the retinoid agent. As is further contemplated, and without wishing to be bound by theory or mechanism, it believed that biochemical chemical pathways related to conditions of interest are impacted in a synergistic manner in the presence of both the imidazoquinoline compound and the retinoid agent (e.g., imiquimod and tazarotene), such that the imidazoquinoline compound has improved efficacy in the presence of the retinoid agent and, similarly, the retinoid agent has improved efficacy in the presence of the imidazoquinoline compound.

INCORPORATION BY REFERENCE

All publications, patents, and patent applications mentioned in this specification, including those set forth in the following list, are herein incorporated by reference to the same extent as if each individual publication, patent, or patent application was specifically and individually indicated to be incorporated by reference.

REFERENCES

DePaula, Martins, and Bentley, "Development and validation of HPLC method for imiquimod determination in skin penetration studies," *Biomed Chromatogr* 22(12): 1416-23 (2008).

Jackson and Callen, (In Press) Chapter 128: Immunomodulators. In Bolognia, Jorizzo, and Rapini *Dermatology*, 3d. Edition.

Owens M L, Bridson W E, Smith S L, Myers J A, Fox T L, and Wells T M, "Percutaneous penetration of Aldara cream, 5% during the topical treatment of genital and perianal warts," *Prim Care Update Ob Gyns.* 5(4):151 (1998).

Skelly, J. P., Shah, V. P., Maibach, H. I., Guy, R. H., Wester, R. C., Flynn, G. L. and Yacobi, A. (1987). "FDA and AAPS report of the workshop on principles and practices of in-vitro percutaneous penetration studies: Relevance to bioavailability and bioequivalence." *Pharmaceutical Research* 4(3): 265-267.

What is claimed is:

1. A composition, comprising: imiquimod and tazarotene, wherein the ratio of the concentration of tazarotene to the concentration of imiquimod is less than 1:5.

2. The composition according to claim 1, wherein the imiquimod is at a final concentration between about 8% (wt/wt) and about 0.1% (wt/wt).

3. The composition according to claim 1, wherein the tazarotene is at a final concentration of about 0.1% (wt/wt) and about 0.001% (wt/wt).

4. The composition of claim 1, wherein the tazarotene is provided in the composition at a final concentration of less than about 0.1% (wt/wt) to about 0.001% (wt/wt).

5. The composition of claim 4, wherein the imiquimod is provided in the composition at a final concentration of less than about 8% (wt/wt) and about 0.1% (wt/wt).

6. The composition of claim 1, wherein the tazarotene is provided in the composition at a final concentration of about 0.01% (wt/wt) to about 0.001% (wt/wt).

7. The composition of claim 6, wherein the imiquimod is provided in the composition at a final concentration of less than about 8% (wt/wt) and about 0.1% (wt/wt).

8. The composition of claim 1, wherein the imiquimod is provided in the composition at a final concentration of less than about 8% (wt/wt) and about 0.1% (wt/wt).

9. The composition of claim 1, wherein the ratio of the concentration of tazarotene to the concentration of imiquimod is less than 1:10.

10. The composition of claim 1, wherein the composition is substantially stable at a temperature of 50° C. for a period of four (4) weeks.

11. A method for the treatment of a condition affecting skin and/or a mucosal surface of a subject, comprising: administering an effective amount of the composition according to claim 1 to the subject in need thereof.

12. The method of claim 1, wherein the composition is administered to an affected site on the skin and/or mucosal surface of the subject.

13. The method of claim 1, wherein the composition is administered topically.

14. The method of claim 1, wherein the composition is administered by intralesional injection.

15. The method of claim 1, wherein the condition is selected from a wart, Molluscum contagiosum, a keloid, and a skin cancer.

16. The method of claim 1, wherein the condition is a keloid scar or a hypertrophic scar.

17. The method of claim 1, wherein the condition is a skin cancer.

18. The method of claim 17, wherein the skin cancer is selected from melanoma and non-melanoma skin cancers, actinic keratoses, basal cell carcinomas, squamous cell carcinoma in-situ or Bowen's disease, melanoma in-situ, and other unresectable carcinomas.

19. The method of claim 17, wherein the skin cancer is selected from: cutaneous T-cell lymphoma, extramammary Paget's disease, lentigo maligna, cutaneous melanoma metastases, and cutaneous leishmaniasis.

20. The method of claim 1, wherein the subject is receiving antirejection therapy following a transplant.

\* \* \* \* \*